United States Patent
Daniloff et al.

(10) Patent No.: US 9,011,894 B2
(45) Date of Patent: Apr. 21, 2015

(54) STERILE HYALURONIC ACID POLYMER COMPOSITIONS AND RELATED METHODS

(75) Inventors: George Y. Daniloff, Los Altos, CA (US); Robert C. Spiro, Half Moon Bay, CA (US); David M. Gravett, Mountain View, CA (US); Patrick J. Hillas, San Francisco, CA (US); Pingren He, Sunnyvale, CA (US)

(73) Assignee: Carbylan Therapeutics, Inc., Palo Alto, CA (US)

( * ) Notice: Subject to any disclaimer, the term of this patent is extended or adjusted under 35 U.S.C. 154(b) by 1358 days.

(21) Appl. No.: 12/165,607

(22) Filed: Jun. 30, 2008

(65) Prior Publication Data

US 2009/0017091 A1 Jan. 15, 2009

Related U.S. Application Data

(60) Provisional application No. 60/947,357, filed on Jun. 29, 2007.

(51) Int. Cl.

| A61F 2/00 | (2006.01) |
|---|---|
| A61K 9/14 | (2006.01) |
| A01N 43/04 | (2006.01) |
| A61L 27/52 | (2006.01) |
| A61L 27/20 | (2006.01) |
| A61L 27/50 | (2006.01) |

(52) U.S. Cl.
CPC ............... *A61L 27/52* (2013.01); *A61L 27/20* (2013.01); *A61L 27/50* (2013.01)

(58) Field of Classification Search
CPC .......... A61L 27/52; A61L 27/20; A61L 27/50
USPC .................... 424/423, 488; 514/54
See application file for complete search history.

(56) References Cited

U.S. PATENT DOCUMENTS

| 4,263,253 A | 4/1981 | Pilz et al. |
|---|---|---|
| 5,356,883 A | 10/1994 | Kuo et al. |
| 5,502,081 A | 3/1996 | Kuo et al. |
| 5,621,093 A | 4/1997 | Swann et al. |
| 5,834,444 A * | 11/1998 | Falk et al. ............ 514/54 |
| 5,874,417 A | 2/1999 | Prestwich et al. |
| 6,013,679 A | 1/2000 | Kuo et al. |
| 6,056,970 A | 5/2000 | Greenawalt et al. |
| 6,149,864 A | 11/2000 | Dillow et al. |
| 6,383,344 B1 | 5/2002 | Miller et al. |
| 6,537,979 B1 | 3/2003 | Kuo et al. |
| 6,548,081 B2 | 4/2003 | Sadozai et al. |
| 6,620,927 B2 | 9/2003 | Bulpitt et al. |
| 6,884,788 B2 | 4/2005 | Bulpitt et al. |
| 6,891,035 B2 | 5/2005 | Ljungquist |
| 2005/0154196 A1 | 7/2005 | Maeda et al. |
| 2005/0176620 A1 | 8/2005 | Prestwich et al. |
| 2005/0277577 A1 * | 12/2005 | Hunter et al. ............ 514/2 |
| 2006/0292030 A1 | 12/2006 | Odermatt et al. |
| 2007/0009578 A1 | 1/2007 | Moller et al. |

FOREIGN PATENT DOCUMENTS

| EP | 1 543 842 A1 | 6/2005 |
|---|---|---|
| WO | WO 2005/056608 A1 | 6/2005 |
| WO | WO 2005056608 A1 * | 6/2005 |
| WO | WO 2006/124988 A2 | 11/2006 |
| WO | WO 2008/098019 A2 | 8/2008 |

OTHER PUBLICATIONS

TESS report for CARBYLAN trademark information. Last accessed Dec. 4, 2010.*
The International Search report and Written Opinion for PCT application PCT/US2008/008157, search report dated Jan. 19, 2009, 18 pages (2009).
Ghosh, K. et al., "Rheological characterization of in situ cross-linkable hyaluronan hydrogels", *Biomacromolecules*, 6(5):2857-2865 (2005).
Liu, Y. et al., "Reduced postoperative intra-abdominal adhesions using Carbylan-SX, a semisynthetic glycosaminoglycan hydrogel", *Fertility and Sterility*, 87(4):940-948 (2007).
Prestwich, G.D. et al., "Injectable Synthetic Extracellular Matrices for Tissue Engineering Repair", *Advances in Experimental Medicine and Biology*, 585:125-133 (2006).
Samoilenko, I.I. et al., Database WPI Week 199640, Thomson Scientific, Lodon GB, *Epidemiology Microbiology Research Institute*, Abstract (1995).
Shu, X.Z. et al., "Disulfide cross-linked hyaluronan hydrogels", *Biomacromolecules*, 3(6):1304-1311 (2002).
Duflo, S. et al, "Vocal Fold Tissue Repair In Vivo Using a Synthetic Extracellular Matrix", *Tissue Engineering*, 12(8):2171-2180 (2006).
Liu, Y. et al, "Osteochondral defect Repair with Autologous Bone Marrow-Derived Mesenchymal Stem Cells in an Injectable, In Situ, Cross-Linked Synthetic Extracellular Matrix", *Tissue Engineering*, 12(12):3405-3416 (2006).
Sparer, R.V. et al., Controlled Release from Glycosaminoglycan Drug Complexes, Chapter 6, pp. 107-119, in T. J. Roseman et al., *Controlled Release Delivery Systems*, Marcel Dekker, Inc., New York (1983).
Zahraoui, C., and Sharrock, P., "Influence of Sterilization on Injectavble Bone Biomaterials", *Bone*, 25(2 Supp. 1):63S-65S (1999).

* cited by examiner

*Primary Examiner* — Cherie M Stanfield
(74) *Attorney, Agent, or Firm* — Susan T. Evans; McDermott Will & Emery LLP

(57) ABSTRACT

The present application provides sterile hyaluronic polymer compositions than are useful, e.g., as medical devices, biomedical adhesives, and sealants. Generally, provided are sterile dry compositions comprising a thiol-derivatized hyaluronic acid and one or more stabilizing excipients. Also provided are related kits and methods. The compositions described herein are particularly robust to sterilizing irradiation, and substantially maintain both their molecular weight and gelation parameters such as gelation time after sterilization, such that such sterile compositions are capable of hydrogel formation.

20 Claims, No Drawings

STERILE HYALURONIC ACID POLYMER COMPOSITIONS AND RELATED METHODS

CROSS-REFERENCE TO RELATED APPLICATIONS

This application claims the benefit of priority to Provisional Patent Application No. 60/947,357, filed Jun. 29, 2007, which is incorporated herein by reference in its entirety.

FIELD

The disclosure relates generally to sterile dry polymer compositions comprising polysaccharides such as hyaluronic acid, kits containing such dry sterile compositions, and related methods for their preparation and use. The sterile dry polymer compositions are useful upon hydration as, for example, medical devices, biomedical adhesives and sealants, among other uses. More particularly, the application provides methods of sterilizing polysaccharides, and in particular, reactive polysaccharides in dry form, using, for example, electron beam or gamma irradiation to provide sterile compositions that are, for example, water-soluble and capable of hydrogel formation.

BACKGROUND

Many polymeric materials, including hyaluronic acid, derivatized forms thereof, and its conjugates, can be used as injectable biomaterials, as well as in medical devices and implantable materials. Typically, use as an injectable material, medical device, implantable material or the like requires sterilization prior to storage or use. Unfortunately, many polymeric materials are fragile to common sterilization procedures. Sterilization can often lead to pronounced changes in the physico-chemical properties of the polymer post-sterilization, such that the resulting sterile polymer composition is rendered unsuitable for its intended use.

Sterilization methods that are currently applied to medical materials include, for example, heat treatment, high-pressure vapor sterilization (e.g. autoclave sterilization), ethylene oxide gas (EOG) sterilization, supercritical carbon dioxide sterilization and radiation sterilization. See for example, U.S. Pat. No. 6,891,035, U.S. Pat. No. 6,149,864, U.S. Pat. No. 5,621,093, U.S. Pat. No. 4,263,253, and U.S. Patent Publication Nos. US 2006/0292030, and US 2007/0009578. Available sterilization methods are typically assessed in relation to the robustness of the particular composition to be sterilized. For example, high-pressure vapor sterilization may be used for a medical material only to the extent that the material can endure high temperatures and high pressures. However, few biocompatible compositions can endure high temperatures and high pressures. EOG sterilization is useful because the process suppresses the deterioration of the material. However, residual ethylene oxide has an adverse effect on living organisms, such as hemolysis and other toxic reactions.

Many biomaterials have been reported to suffer deleterious effects upon sterilization. For example, chitosan solutions show a dramatic decrease in viscosity after 25-kGy gamma sterilization (Zahraoui, C., Sharrock, P., Bone, 25 (2), Supp. 1, August 1999, p. 63S-65S). Heat sterilization has also been described to degrade chitosan solutions, while ultrafiltration is difficult due to the high viscosity of the material (Zahraoui, ibid). Aqueous co-polylactide solutions show, by capillary electrophoresis, that hydrolysis occurs to liberate monomers following 25-kGy gamma sterilization (Zahraoui, ibid). Additionally, gel exclusion chromatography of gelatin reveals crosslinking of the chains due to irradiation (Zahraoui, ibid). Further, monomers used in standard acrylic cements are typically sterilized by ultrafiltration because they are unstable upon irradiation.

Based upon the foregoing, it can be seen that sterilization of polymer-based materials is not at all routine, and provides numerous challenges to arrive at a substantially intact sterile product, particularly in the case of a reactive polymer.

SUMMARY OF THE INVENTION

In a first aspect, provided herein is a sterile dry polymer composition that is soluble in aqueous solution. The sterile dry polymer composition comprises a reactive polysaccharide such as a thiol-derivatized hyaluronic acid and one or more stabilizing excipients. Generally, the reactive polysaccharide has a molecular weight in the range of 50,000 daltons to 1,000,000 daltons as determined by multi-angle light scattering, and is capable of crosslinking to form a hydrogel.

In one embodiment, the reactive polysaccharide is a thiol-derivatized hyaluronic acid.

In yet another embodiment, the sterile dry polymer composition comprises a thiol-derivatized hyaluronic acid that has a defined molecular weight prior to sterilization, and a molecular weight after sterilization by irradiation that is within 60% of the defined molecular weight.

In an alternative embodiment of the foregoing, the molecular weight after sterilization by irradiation is within about 70% of the defined molecular weight. In yet another embodiment, the molecular weight after sterilization by irradiation is within about 80% of the defined molecular weight, or is even within about 90% of the defined molecular weight.

In a second aspect, provided herein is a sterile dry polymer composition that is soluble in aqueous solution, where the composition comprises a thiol-derivatized hyaluronic acid having a molecular weight in the range of 50,000 daltons to 1,000,000 daltons as determined by multi-angle light scattering, and one or more stabilizing excipients, where the composition possesses an initial gelation time that changes by no more than about ±25% upon storage at 25° C. in a sealed foil pouch for a period of one month.

In yet another embodiment of the foregoing, the composition possesses an initial gelation time that changes by no more than about +20% upon storage at 25° C. in a sealed foil pouch for a period of one month.

In yet a further embodiment, the composition possesses an initial gelation time that changes by no more than about +15% upon storage at 25° C. in a sealed foil pouch for a period of one month.

In yet a third aspect, provided herein is a method of preventing, ameliorating, or treating a defect or condition in bone, teeth, nerves, cartilage, artery, soft tissue, or other tissue, where the method comprises the steps of mixing a dry composition comprising a thiol-derivatized hyaluronic acid polymer with a pharmaceutically acceptable buffer solution to form a gel, and injecting or implanting the gel onto or into bone, teeth, nerves, cartilage, blood vessels, soft tissues or other tissues of a mammalian subject, the improvement comprising, in the mixing step, a sterile dry polymer composition as follows. The sterile dry polymer composition is soluble in aqueous solution and comprises a thiol-derivatized hyaluronic acid having a molecular weight in the range of 50,000 daltons to 1,000,000 daltons, and one or more stabilizing excipients, where (i) the thiol-derivatized hyaluronic acid has a defined molecular weight as determined by multi-angle light scattering prior to sterilization, and a molecular weight after sterilization by irradiation that is within 60% of the defined molecular weight, and (ii) the composition possesses an initial gelation time that changes by no more than about ±25% upon storage at 25° C. in a sealed foil pouch for a period of one month.

In yet another, fourth aspect, provided herein is a kit comprising a first sealed container comprising a dry composition comprised of a thiol-derivatized hyaluronic acid polymer, a second sealed container comprising a pharmaceutically acceptable buffer solution, and optionally, a third container that is empty or comprises saline, the improvement comprising, in the first sealed container, a sterile dry polymer composition that is soluble in aqueous solution and comprises a thiol-derivatized hyaluronic acid having a molecular weight in the range of 50,000 daltons to 1,000,000 daltons as determined by multi-angle light scattering, and one or more stabilizing excipients, wherein (i) the thiol-derivatized hyaluronic acid has a defined molecular weight as determined by multi-angle light scattering prior to sterilization, and a molecular weight after sterilization by irradiation that is within 60% of the defined molecular weight, and (ii) the composition possesses an initial gelation time that changes by no more than about ±25% upon storage at 25° C. in a sealed foil pouch for a period of one month.

In an embodiment related to the fourth aspect, the kit further comprises an active agent in one of the first, second, or third sealed containers, or in a fourth sealed container.

In yet another embodiment related to the fourth aspect, the first, second, and third containers are each a syringe.

In a fifth aspect, provided herein is a method for forming a sterile dry polymer composition. The method comprises (i) providing a sealed container comprising a dry polymer composition comprised of a thiol-derivatized hyaluronic acid and one or more stabilizing excipients, wherein the thiol-derivatized hyaluronic acid has a defined molecular weight as determined by multi-angle light scattering, and (ii) subjecting the sealed container to electron beam or gamma irradiation at a dose and under conditions sufficient to sterilize the contents of the sealed container, to thereby provide a sterile dry polymer composition that is soluble in aqueous solution and capable of crosslinking to form a hydrogel, wherein the molecular weight of the thiol derivatized hyaluronic acid has a molecular weight in the range of 50,000 daltons to 1,000,000 daltons In an embodiment related to the fifth aspect, the thiol-derivatized hyaluronic acid has a molecular weight after sterilization by irradiation that is within 60% of the defined molecular weight prior to sterilization.

In a sixth aspect, provided is yet another method for forming a sterile dry polymer composition. The method comprises (i) providing a sealed container comprising a dry polymer composition comprised of a thiol-derivatized hyaluronic acid and one or more stabilizing excipients, wherein the composition possesses an initial gelation time, and (ii) subjecting the sealed container to electron beam or gamma irradiation at a dose and under conditions sufficient to sterilize the contents of the sealed container, to thereby provide a sterile dry polymer composition that is (a) soluble in aqueous solution, and (b) possesses a gelation time that is changed by no more than about ±25% upon storage at 25° C. in a sealed foil pouch for a period of one month.

In one embodiment directed to each of the fifth and sixth aspects which provide a method for forming a sterile dry polymer composition, the irradiation is electron beam irradiation at a dosage ranging from 0.5 to 10.0 MRad.

In yet another embodiment directed to each of the fifth and sixth aspects which provide a method for forming a sterile dry polymer composition, the electron beam irradiation dosage ranges from about 1.5 to 5.0 MRad.

In yet another embodiment directed to each of the fifth and sixth aspects which provide a method for forming a sterile dry polymer composition, the irradiation is gamma irradiation at a dosage ranging from about 0.5-10.0 MRad.

In yet another embodiment directed to each of the fifth and sixth aspects which provide a method for forming a sterile dry polymer composition, the gamma irradiation is in a dosage range from about 1.5 to 5.0 MRad.

Embodiments directed to each and every of the foregoing aspects provided herein include the following:

In one embodiment directed to each and every of the foregoing aspects as applicable, the combination of stabilizing excipients is selected from a chelating agent, a radical scavenger, an anti-oxidant, a solubilizer, and a thiol.

In yet another embodiment, the one or more stabilizing excipients is selected from ascorbic acid, dithiothreitol (DTT), ethylenediamine tetraacetic acid (EDTA), and sucrose.

In yet a further embodiment, the one or more stabilizing excipients comprise ascorbic acid, dithiothreitol, and EDTA.

In yet an additional embodiment, the sterile dry polymer composition or pre-sterilized composition comprises one or more of the following amounts of stabilizing excipient on a per weight basis relative to the thiol-derivatized hyaluronic acid: from about $1.0 \times 10^{-3}$ to 0.10 times dithiothreitol, from about $2.1 \times 10^{-3}$ to 0.20 times EDTA, from about 0.06 to 6 times sucrose, and from about 0.06 to 6 times ascorbic acid.

In yet another embodiment, the thiol-derivatized hyaluronic acid is Carbylan™-S or a derivatized form thereof.

In a further embodiment, the thiol-derivatized hyaluronic acid comprised in the sterile dry polymer composition is not crosslinked or is lightly crosslinked.

In yet an additional embodiment, the thiol-derivatized hyaluronic acid in the sterile dry polymer composition has a molecular weight ranging from about 90,000 daltons to about 300,000 daltons.

In yet another aspect, provided herein is the use of a sterile dry polymer composition as described herein for mixing with a pharmaceutically acceptable buffer solution to form a hydrogel for injecting or implanting onto or into bone, teeth, nerves, cartilage, blood vessels, soft tissues or other tissues of a mammalian subject.

Additional embodiments of the compositions, methods, kits, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

This application contains no drawings.

DETAILED DESCRIPTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety.

DEFINITIONS

It must be noted that, as used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

Unless specifically noted otherwise, definitions of the terms herein are standard definitions used in the arts of organic synthesis, and polymer and pharmaceutical science.

In describing and claiming the present invention, the following terminology will be used in accordance with the definitions described below.

A "biocompatible polymer" is a polymer having degradation products that are compatible with living tissue, or that may have beneficial biological properties. The biocompatible polymer may be biocompatible in itself, and/or may be synergistically biocompatible when employed in conjunction with a biologically active agent.

The term "bioresorbable polymer" means a polymer that is capable of being metabolized, degraded or broken down and resorbed and/or eliminated through normal biological actions or processes and excretory processes by the body. Such metabolized or break down products are preferably substantially non-toxic to the body, and such products may themselves be bioactive. As used herein, the bioresorbable polymers of the present application may also be bioactive polymers. See D. D. Allison and K. J. Grande-Allen, Tissue Engineering, Vol. 12, Number 8, 2131-2140 (2006).

The terms "bioabsorbable" or "biodegradable" as used herein interchangeably, refers to the ability of a tissue-compatible material to degrade in the body after implantation into nontoxic products that are eliminated from the body or metabolized. See, for example, Barrows, "*Synthetic Bioabsorbable Polymers*," p. 243, In: HIGH PERFORMANCE BIOMATERIALS—A COMPREHENSIVE GUIDE TO MEDICAL AND PHARMACEUTICAL APPLICATIONS, Michael Szycher, ed., Technomic Publishing, Lancaster, Pa., 1991.

The term "hyaluronic acid polymer" refers to a polymer comprising repeat disaccharide subunits of hyaluronan, where the repeat units may be derivatized at one or more positions of the D-glucuronic acid and/or the D-N-acetylglucosamine unit of the disaccharide repeat subunit. A hyaluronic acid polymer is meant to encompass hyaluronic acid (also referred to as hyaluronan), derivatized hyaluronic acid, salts forms, hyaluronic acid linker complexes, and hyaluronic acid conjugates.

The terms "hyaluronic acid derivative" or "derivatized hyaluronic acid" refers to hyaluronic acid that has been derivatized by reaction with, e.g., one or more small chemical moieties. Typically, derivatized hyaluronic acid is covalently bound to small chemical moieties, and includes generally, for example, thiol-derivatized hyaluronic acid, cysteine-derivatized hyaluronic acid, and more specifically, Carbylan™-S, among others. Such complexes can be non-crosslinked, partially or lightly crosslinked, or crosslinked.

A thiol-derivatized hyaluronic acid polymer refers to a hyaluronic acid polymer as described above having three or more disaccharide repeat units and comprising at least one sulfhydryl(thiol) group.

The term "reactive" refers to a functional group (e.g., present in a polymer) that reacts readily or at a practical rate under conventional conditions of organic synthesis. This is in contrast to those groups that either do not react or require strong catalysts or impractical reaction conditions in order to react (i.e., a "nonreactive" or "inert" group).

The term "hyaluronic acid-linker complex" refers to hyaluronic acid that is covalently bound to a linker, defined herein. Such complexes can be non-crosslinked, partially crosslinked or crosslinked.

"Molecular mass" or molecular weight, as used herein, in the context of a water-soluble polymer such as thiol-derivatized hyaluronic acid, refers to the nominal average molecular mass of a polymer determined by multi angle light scattering. Molecular weight can be expressed as either a number-average molecular weight or a weight-average molecular weight. Unless otherwise indicated, all references to molecular weight herein refer to the number-average molecular weight. The polymers described herein are typically polydisperse (i.e., number-average molecular weight and weight-average molecular weight of the polymers are not equal), and possess polydispersity values such as less than about 1.6, less than about 1.4, less than about 1.3, and less than about 1.2.

The term "hydrogel" refers to a water-containing three dimensional hydrophilic polymer network or gel in which the water is the continuous phase and in which the water content is greater than 50% (w/w). Hydrogels typically exhibit excellent biocompatibility. Under certain conditions, the sterile dry thiol-derivatized hyaluronic acid polymers described herein are capable of forming hydrogels. The hydrogels described herein typically do not require the incorporation of additional cross-linking reagents to form a hydrogel, although cross-linking accelerants may be employed.

The term "terminal sterilization" as used herein typically describes a process whereby a composition, which may or may not be presterilized, but is typically unsterilized, is filled and sealed in a container, and then subjected to a final sterilization step.

A "sterile" composition is one that is free of viable microbes as determined using the USP sterility test. See "The United States Pharmacopeia", 30th Revision, The United States Pharmacopeial Convention: 2008.

The term "initial gelation time", determined, e.g., as described in Examples 7 and 9, refers to the initial gelation time determined within 14 days following terminal sterilization of a dry polymer composition as provided herein; such time point is considered to be T=0 or the initial time point and the starting point of a stability study. All time points measured subsequent to T=0 are referenced back to the T=0 time point, e.g., 1 week from the T=0 time point, 2 weeks from the T=0 time point, etc.

The term "gel point" refers to the point where the storage (G') and loss (G") modulus have the same value as measured at a constant frequency using an AR550 rheometer (TA Instruments).

The term "gel time" refers to the time that it takes to reach the gel point.

The term "gel" refers to a material in which the storage (G') is greater than the loss (G") modulus as measured at a constant frequency using an AR550 rheometer (TA Instruments).

The term "crosslinkable" refers to the ability of a material to form covalent bonds resulting in the formation of a gel.

The term "hydrophobic" refers to compounds or compositions which lack an affinity for water.

The term "polyethylene glycol" or "PEG" is sometimes also referred to as poly(ethylene oxide) (PEO) or poly(oxyethylene). These terms may be used interchangeably.

The term "polyanionic polysaccharide" (PAS) means a polysaccharide, including non-modified as well as chemical derivatives thereof, that contains more than one negatively charged group (e.g., carboxyl groups at pH values above about 4.0) and includes salts thereof, such as sodium or potassium salts, and alkaline earth metal salts such a calcium or magnesium salts.

The term "linker" as used herein means any divalent group or moiety that is capable of linking two biopolymers, such as polysaccharides, hyaluronic acid, hyaluronan, or derivatives thereof, such as Carbylan™-S polymers. Thus, such linkers are typically bifunctional.

The term "hydrocarbyl" as used herein means the monovalent moiety obtained upon removal of a hydrogen atom from a parent hydrocarbon. Representative hydrocarbyl groups are alkyl of 1 to 20 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aryl of 6 to 12 carbon atoms, inclusive, such as phenyl, tolyl, xylyl, naphthyl, biphenyl, tetraphenyl and the like; aralkyl of 7 to 12 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 10 carbon atoms, inclusive, such as vinyl, allyl, butenyl, pentenyl, hexenyl, octenyl, nonenyl, decenyl, undecenyl, dodecenyl, tridecenyl, pentadecenyl, octadecenyl, pentacosynyl and isomeric forms thereof. Preferably, the hydrocarbyl group has 1 to 20 carbon atoms, inclusive.

The term "heterocarbyl" as used herein means a hydrocarbyl group that contains a heteroatom such as oxygen, sulfur, or nitrogen incorporated within the chain or ring. Examples of monovalent heterocarbyls include acyl, acyloxy, alkoxyacyl, heterocyclyl, heteroaryl, aroyl, benzoyl, dialkylamino, hydroxyalkyl, and so on.

The term "substituted hydrocarbyl and heterocarbyl" as used herein means the hydrocarbyl or heterocarbyl moiety as previously defined wherein one or more hydrogen atoms have been replaced with a chemical group, which does not adversely affect the desired preparation of the modified polysaccharide. Representative of such replacement groups are amino, phosphino, quaternary nitrogen (ammonium), quaternary phosphorous (phosphonium), hydroxyl, amide, alkoxy, mercapto, nitro, alkyl, halo, sulfone, sulfoxide, phosphate, phosphite, carboxylate, carbamate groups and the like.

The term "partially or lightly crosslinked" as used herein means less than 1% of the available crosslinkable sites are present in crosslinked form.

The term "crosslinked" as used herein means that greater than 1% of the available crosslinkable sites have formed crosslinks.

The term "drug," or "pharmaceutically active agent" or "bioactive agent," or "active agent" as used interchangeably, means any organic or inorganic compound or substance having bioactivity and adapted or used for therapeutic purposes. Proteins, hormones, anti-cancer agents, small molecule chemical compounds and mimetics, oligonucleotides, DNA, RNA and gene therapies are included under the broader definition of "drug". As used herein, reference to a drug, as well as reference to other chemical compounds herein, is meant to include the compound in any of its pharmaceutically acceptable forms, including isomers such as diastereomers and enantiomers, salts, solvates, and polymorphs, particular crystalline forms, as well as racemic mixtures and pure isomers of the compounds described herein, where applicable.

The term "solid" as used herein, means a non-fluid substance, including crystalline forms, their polymorphs, non-crystalline amorphous substances, precipitates, and particles, or the like. Each of these solid forms may vary in size, from about 0.01 microns to 2,000 microns, for example, from about 0.01 microns to 1 micron, from 1 micron to 100 microns, from 100 microns to 1,000 microns, from 1000 microns to 2000 microns, from 1100 microns to 1500 microns, and from 1500 microns to 2000 microns.

The term "sponge" as used herein means a porous structure.

The phrase "soluble in aqueous solution" refers to a composition or compound that is capable of dissolving in aqueous buffer such as phosphate buffered saline at a concentration of at least 0.1 mg/mL at room temperature.

The phrase "dry form" refers to a solid having a moisture content below about 10% by weight. As disclosed herein, the dry form may be for example, a powder, flake, granule, pellet, sponge, microsphere, sheet or film.

"Peptide," "polypeptide," "oligopeptide" and "protein" are used interchangeably when referring to peptide or protein drugs (or as bioactive agents), and shall not be limited as to any particular molecular weight, peptide sequence or length, field of bioactivity or therapeutic use, unless specifically stated otherwise.

The term "pharmaceutically acceptable salts" refer to salts or complexes that retain the desired biological activity of the compounds (or drugs or biologically active agents) of the present application and exhibit minimal undesired toxicological effects. A reference to a polymer, drug, molecule or chemical entity is meant to encompass its pharmaceutically acceptable salt forms. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art.

"Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e, to a degree of 85% or greater) in reference to the feature or entity.

The term "about", particularly in reference to a given quantity, is meant to encompass deviations of plus or minus five percent.

Additional definitions may also be found in the sections which follow.

Overview

The present application is based, at least in part, on the inventors' discovery of a method by which reactive polymers such as thiol-derivatized hyaluronic acid can be successfully sterilized—whilst maintaining certain properties of the polymers related to hydrogel formation and ultimate product performance. The discovery is important in many respects. First, the method utilized does not require aseptic or clean room conditions to prepare the final sterile polymer compositions. Such avoidance of aseptic processing is extremely beneficial and cost-saving from a manufacturing standpoint—as the need for a clean area, air filtration system, particle monitoring, sampling, and the like is circumvented. Rather than rely on aseptic processing, the instant method utilizes a terminal sterilization step, where sterilization occurs subsequent to the preparation and packaging of the subject polymer composition. In this way, sterilization can occur in-line or off-line in the manufacturing process—adding to manufacturing process flexibility.

The current method involves terminal sterilization of polymer compositions in a dry form. The dry compositions that are subject to sterilization comprise a reactive polymer. Reactive polymers, such as those described herein, e.g., thiol-derivatized hyaluronic acid, are extremely difficult to sterilize due to their reactivity. Such reactivity often leads to premature cross-linking and/or excessive degradation of the reactive polymer upon sterilization, particularly by irradiation. Premature crosslinking of the sterile composition can, depending upon the degree, lead to a sterile product having altered dissolution properties relative to the non-sterilized product—thus adversely impacting product performance upon mixing with buffer (wetting) to form a hydrogel, or in vivo. Extensive premature crosslinking prior to mixing with buffer can also significantly decrease gelation time—another indicator of impact on product performance. Degradation of the instant reactive polymers upon sterilization will typically lead to increased gelation times, again indicating a potential for failure of the resulting sterilized lot.

The current process employs terminal sterilization by irradiating a dry composition comprising a reactive polymer such as a thiol-derivatized hyaluronic acid and one or more stabilizing excipients. The resulting sterile compositions are soluble in aqueous solution (thus indicating the absence of a significant degree of crosslinking upon sterilization), and are capable of crosslinking to form a hydrogel. As can be seen in the supporting examples (Example 6, Table 1), in the absence of one or more stabilizing excipients, upon sterilization by gamma irradiation, an exemplary formulation of Carbylan-™-S exhibited a loss in molecular weight from 200,000 daltons pre-sterilization to 12,000 post-sterilization. However, incorporation of one or more stabilizing excipients (to be described more fully below), results in a substantial improvement in reduction of molecular weight (that is to say, the significant if not near total prevention of reduction in molecular weight). Indeed, in one instance, the molecular weight of the reactive polymer remained substantially unchanged following sterilization by irradiation (sample 6). The method provided herein provides sterile dry compositions that are water soluble and that possess molecular weight and gelation time characteristics that are substantially unchanged relative to the pre-sterilized composition.

The features of the method and related compositions, kits, and the like will now be discussed in greater detail below.

Method of Sterilization

The instant method comprises a terminal sterilization step whereby a dry composition is filled and preferably sealed in a container, and then subjected to a sterilization step. Preferably, sterilization is by irradiation.

One method of sterilizing a biocompatible composition as provided herein is by radiation sterilization. Such radiation includes α-rays, β-rays, γ-rays, neutron beams, electron beams, and X-rays. Preferably, γ-ray sterilization or electron beam sterilization is employed. Illustrative dosages include the following: from about 0.5-10 MRad (5-100 kGy), from about 1.5-5.0 MRad (10-50 kGy) or about 2-4 MRad (20-40 kGy) of radiation. For example, the γ-ray sterilization or electron beam sterilization is carried out at about one of the following dosages, in kGY: 10, 15, 20, 25, 30, 35, 40, 45 or 50. See, e.g., Example 6, in which an irradiating dose of 20 kGy was used, and Examples 7 and 8, where dosages of 20, 25, and 30 kGy were employed. Example 9 demonstrates the use of irradiating dosage of 21, 28, and 31 kGy. Generally the dose of electron beam or gamma radiation will range from about 10 to 50 kGy or from 20 to 40 kGy.

The dose of radiation is also determined based on the bioburden level (initial contamination) of the pre-sterilized composition. The exposure time will depend upon the nature of the composition, the strength of the beam, and on the conveyor speed, among other variables, and is typically less than one minute; generally in the range of tenths of a second to several seconds. Dosimeters may be used to determine the optimal exposure times of the particular sample or composition being irradiated.

The temperature of the sterilization procedure may range from about 2° to 50° C., or about 15° to 40° C. or about 20° to 30° C. Typically, irradiation is carried out under ambient conditions.

Preferably, the dry composition is sterilized to provide a Sterility Assurance Level (SAL) of at least $10^{-3}$, or at least $10^{-4}$, or even at least $10^{-5}$. In some instances, a sterile composition as provided herein may possess a Sterility Assurance Level is at least $10^{-6}$ (that is a probability of a nonsterile unit of greater than one in a million).

The composition of the present application may be contained in any type of at least partially electron beam or gamma ray permeable container, including, but not limited to, glass, plastic, foil and film-formed packages. In alternate embodiments, the container may be sealed, or may have an opening. Examples of glass and, in some cases, plastic containers include, but are not limited to, ampules, vials, syringes (single, dual or multiplets), pipettes, applicators, tubes and the like.

For example, the container may be a syringe, or a syringe that includes a syringe cap that is optionally vented. Examples of vented syringe caps include Vented FLL cap 3 micron filter (Qosina, P/N 12089), a Female Luer cap—vented hex luer fit (Qosina, P/N 6570), and a Luer tip syringe cap (Value Plastics (Fort Collins, Colo.), P/N VPM0480201N).

Containers such as but not limited to those described above may also be further packaged and sealed, for example in a pouch such as a sealed foil pouch. Packaging materials for use in the pharmaceutical and medical industry are well known. Containers such as those described in "*Pharmaceutical Packaging Technology*", Dean, D. A., et al., Ed., Taylor & Francis, Inc., 2000, as applicable for compositions of the type provided herein are contemplated for use in the present method and for the compositions and kits provided herein.

The penetration of electron beam or gamma irradiation is generally a function of the packaging material selected. In certain application, if it is determined that there is insufficient penetration from the side of a stationary electron beam or gamma ray, the container may be flipped or rotated to achieve adequate penetration. Alternatively, the electron beam or gamma ray source can be moved about a stationary package or container. In order to determine the dose distribution and dose penetration in product load, a dose map can be performed. A dose map may be used to identify the minimum and maximum dose zone for a particular product, package or container. In certain embodiments, after the container containing the polymer composition is sterilized, for example, with electron beam or gamma irradiation, the container may be subjected to additional sterilization. For example, the container may be placed in a kit with other components as disclosed herein that may require sterilization. In this process, the entire kit may then be sterilized. For example, the entire kit may be further sterilized by chemical (e.g., with ethylene oxide or hydrogen peroxide vapor), physical (e.g., dry heat) or other techniques such as microwave irradiation, electron beam or gamma irradiation.

Polymers, and related compositions for use in the sterilization method provided herein will now be more fully described.

Reactive Polymers and Related Compositions
Bioresorbable Polymers

Various bioresorbable or biodegradable polymers may be employed in the present method and contained in the resultant sterile dry compositions. As mentioned above, preferably, such polymers are reactive, that is, contain one or more reactive functionalities.

Biodegradable or bioabsorbable polymers suitable for use in the instant method include polysaccharides such as glycosaminoglycans, poly(N-acetylglucosamine), chitin, chitosan, cellulose, cellulose acetate, cellulose butyrate, cellulose acetate butyrate, cellophane, cellulose nitrate, cellulose propionate, cellulose ethers, and derivatives, analogs, homologues, copolymers and combinations thereof.

Preferably, the polymer is a polyanionic polysaccharide (PAS). Non-exclusive examples of polyanionic polysaccharides include, for example, hyaluronic acid (HA), carboxymethylcellulose (CMC), carboxymethylamylose (CMA), chondroitin-4-sulfate, chondroitin-6-sulfate, dermatan sulfate, dermatin-6-sulfate, heparin sulfate, heparin, keratin sulfate and their derivatives, and combinations thereof. Such polymers are known in the art, and described, for example, in U.S. Pat. No. 6,056,970. Other biodegradable polymers include fibrin, fibrinogen, starch, poly(amino acids); peptides, proteins, gelatin and collagen.

A preferred polymer is hyaluronic acid. Hyaluronic acid is a naturally occurring linear polysaccharide composed of alternating disaccharide units of N-acetyl-D-glucosamine and D-glucuronic acid joined by alternating β 1→3 glucuronidic and β 1→4 glucosaminidic bonds, so that the repeating unit is (1→4)-β-D-GlcA-(1→3)-β-D-GlcNAc. Hyaluronic acid may be used for various medical applications, including for example, drug delivery systems for a broad variety of drugs. Hyaluronic acid is biocompatible, and may be chemically modified and/or cross-linked to form films and gels for a wide variety of uses. The sterilization method described herein results in compositions of hyaluronic acid having increased stability upon and subsequent to sterilization. The sterilization methods of the present application are also readily applicable to recombinant hyaluronic acid polymers, the preparation of which is known to those of skill in the art.

Functionalized polymers may be prepared by appropriate choice of monomers, or by functionalizing a particular precursor polymer. For example, polymers having pendant hydroxyls can be prepared using a hydroxy acid such as maleic or tartaric acid in the synthesis. Similarly, polymers with pendant amines, carboxyls or other functional groups also may be prepared or purchased from a polymer supplier such as CarboMer, Inc. (San Diego, Calif.). Preferably, the polymers are injectable, biodegradable polymers that are capable of hydrogel formation.

Exemplary polymers for use in the methods and compositions described herein include non-crosslinked and partially crosslinked polymers.

The polymers will typically possess a molecular weight in the range of about 1000 to 6,000,000 daltons, or more preferably, from about 5,000 to 3,000,000 daltons, or even more preferably, from about 15,000 to 1,000,000 daltons. Illustrative molecular weight ranges include from about 50,000 daltons to about 1,000,000 daltons, or from about 90,000 daltons to about 300,000 daltons. For example, the polymer may possess one of the following approximate molecular weights, in kilodaltons: 50, 75, 100, 150, 200, 250, 300, 350, 400, 450, 500, 550, 600, 650, 700, 750, 800, 850, 900, or even 1,000.

In preparing a polymer-containing composition for the delivery of a drug, the desired chemical and physical properties of the polymer should be considered. For example, changing the polymer composition can change the physical properties, including the rate of polymer hydrolysis and accordingly, the rate of release of the drug. In certain embodiments, copolymers may be prepared by using mixtures of diols, triol, polyols, diacids, triacids and different monoalkanoyl glycerides to form a polymer composition having the desired composition and properties. Similarly, blends of two or more polymers may be employed to tailor particular polymer properties for different applications. Copolymers containing other linkages, in addition to an ester linkage also may be prepared. Non-exclusive examples of such copolymers include ester-amides, ester-carbonates, ester-anhydrides and ester urethanes.

Biodegradable Polymers with Linkers

The polymer may also comprise hydrazide-reactive groups and/or aminooxy-reactive groups as described in PCT/US/2004/040726 (corresponding to International Patent Publication No. WO 2005/056608), the disclosure of which is incorporated herein by reference in its entirety. Such macromolecules include oligonucleotides, nucleic acids, polypeptides, lipids, glycoproteins, glycolipids polysaccharides, proteins synthetic polymers, and glycosaminoglycans. Preferably, the glycosaminoglycan is hyaluronan. Even more preferably, the polymer is hyaluronic acid derivatized with one or more reactive groups.

In a preferred embodiment, the polymer is thiol-derivatized, such as a thiol-derivatized hyaluronic acid. Exemplary thiol-derivatized hyaluronic acid polymers include those described in U.S. Pat. Nos. 6,884,788; 6,620,927; 6,548,081, 6,537,979; 6,013,679; U.S. Pat. Nos. 5,502,081; and 5,356,883, the contents each of which is incorporated by reference in its entirety.

Additional examples of hyaluronic acid polymers include cysteine-derivatized hyaluronic acid, including but not limited to those polymers disclosed in "*Controlled Release from Glycosaminoglycan Drug Complexes*" R. V. Sparer et al., Chapter 6, pages 107-119, in T. J. Roseman et al., CONTROLLED RELEASE DELIVERY SYSTEMS, Marcel Dekker, Inc., New York (1983).

Examples of preferred polymers include hyaluronic acid derivatized by a pendant thiol group linked to an N-acyl urea group via a hydrocarbyl, aryl, substituted-hydrocarbyl, or substituted aryl group. Illustrative polymers for use in the compositions and methods provided herein include Carbylan™-S (described in detail in International Patent Publication No. WO 2005/056608).

Exemplary polymers are polysaccharides that have a free thiol functional group. The free thiol can be linked to the polysaccharide via a hydrazide linkage. Specific polysaccharides that can be used include but are not limited to chondroitin sulfate, dextran, dermatan, heparan, heparin, dermatan sulfate, heparan sulfate, alginic acid, pectin, chitosan, hyaluronic acid or carboxymethylcellulose. Specific examples of these types of polymers are described in International Patent Publication No. WO 05/056608, U.S. Pat. No. 5,874,417 and U.S. Patent Publication No. 2005/0176620.

Specific examples of such functionalized polysaccharides are shown in Structures X1 to X3.

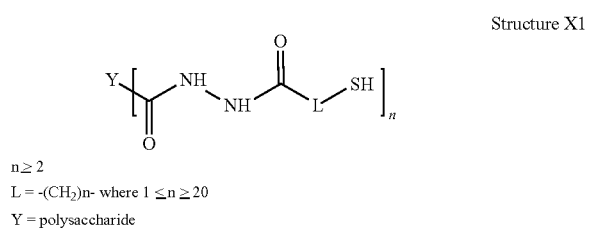

Structure X1 n ≥ 2
L = -(CH$_2$)n- where 1 ≤ n ≥ 20
Y = polysaccharide

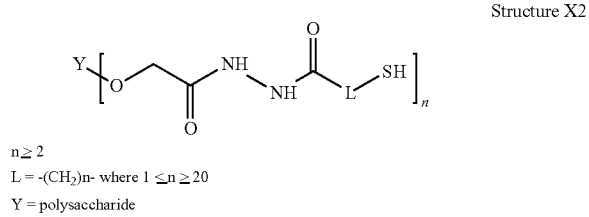

Structure X2 n ≥ 2
L = -(CH$_2$)n- where 1 ≤ n ≥ 20
Y = polysaccharide

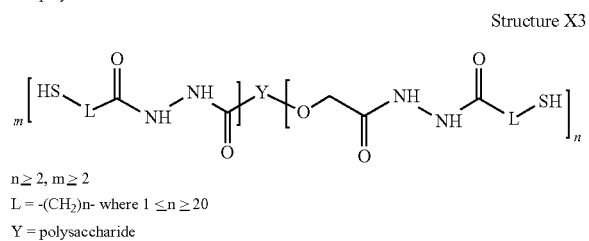

Structure X3 n ≥ 2, m ≥ 2
L = -(CH$_2$)n- where 1 ≤ n ≥ 20
Y = polysaccharide

In one embodiment the thiol functionalized polysaccharide can be hyaluronic acid. Specific examples of functionalized hyaluronic acid are shown in Structures X4 to X6.

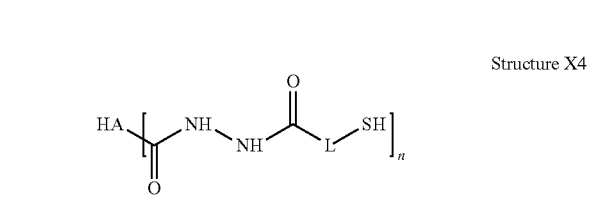

Structure X4 where n≥2, L=—(CH$_2$)$_n$— where 1≤n≥20 and HA=hyaluronic acid where the group is attached through the carboxylic acid of the glucuronic acid unit

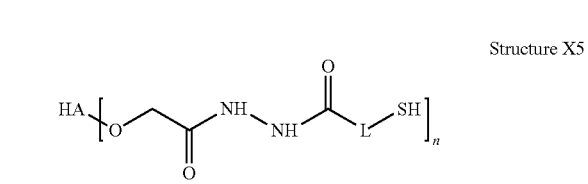

Structure X5

Where n≥2, L=—(CH$_2$)$_n$— where 1≤n≥20, and HA=hyaluronic acid where the group is attached through the 6-hydroxy group of the N-acetyl glucosamine unit

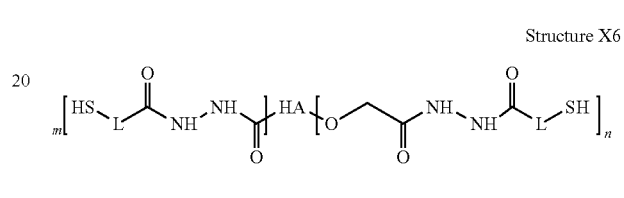

Structure X6 where n≥2, m≥2, L=—(CH$_2$)$_n$— where 1≤n≥20, HA=hyaluronic acid where the ether linkage is through the 6-hydroxy group of the N-acetyl glucosamine unit and the —CO—NH—NH—CO-L-SH linkage is through the carboxylic acid of the glucuronic acid unit.

In one embodiment L is —CH$_2$—CH$_2$— in structures X4 to X6. Examples of these structures are shown in structures X7 to X9.

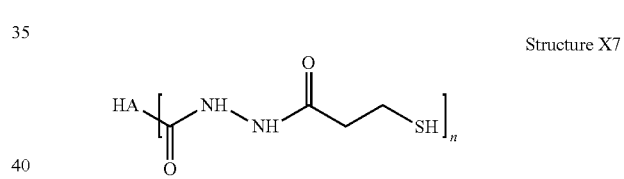

Structure X7 where n≥2 and HA=hyaluronic acid where the group is attached through the carboxylic acid of the glucuronic acid unit;

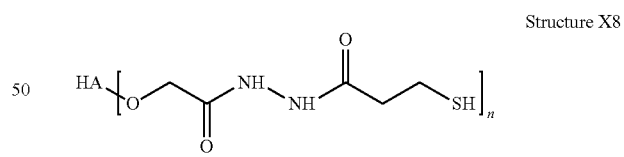

Structure X8 where n≥2 and HA=hyaluronic acid where the group is attached through the 6-hydroxy group of the N-acetyl glucosamine unit;

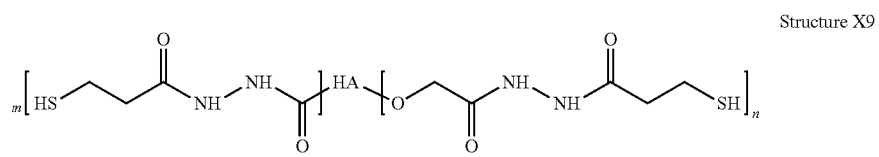

Structure X9 where n≥2, m≥2 and
HA=hyaluronic acid where the ether linkage is through the 6-hydroxy group of the N-acetyl glucosamine unit and the —CO—NH—NH—CO—CH$_2$—CH$_2$—SH linkage is through the carboxylic acid of the glucuronic acid unit.

Additional polymers include hyaluronic acid covalently attached to a linker such as a difunctional acrylate, allyl or methacrylate compound. Representative linkers include, but are not limited to, poly(ethylene glycol)-diacrylate (PEGDA), poly(ethylene glycol)-dimethacrylate (PEGDM), poly(ethylene glycol)-diacrylamide (PEGDAA) and poly (ethylene glycol)-dimethacrylamide (PEGDMA), and derivatives thereof. Additional linkers include dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate, sorbitol acrylate and derivatives thereof.

Further examples of linkers include thiol-containing compounds having two or more thiol groups. Illustrative linkers include dimercaptosuccinic acid, 2,3-dimercapto-1-propanesulfonic acid, dihydrolipoic acid, thiol functionalized dextran, and thiol-functionalized hyaluronic acid. Further examples of such linkers include those described in International Patent Application No. PCT/US2004/040726.

Stabilizing Excipients

The compositions provided herein comprise, in addition to the reactive polymer, one or more stabilizing excipients. As can be seen in the supporting examples, certain types of excipients are effective to stabilize the polymer composition against the harmful effects of sterilizing irradiation, such as reduction in molecular weight, decreased solubility in aqueous solution, and altered gelation times.

Suitable excipient(s) are selected on the basis of compatibility with the reactive polymer, mode of irradiation, and the like. For instance, the excipient should not contribute to the decomposition of the linker, polysaccharide (e.g., hyaluronic acid polymer), and should be compatible to the parameters of sterilizing radiation employed. Further, the excipient should not interfere with or prohibit the subsequent use of the sterilized composition.

Preferred stabilizing excipients include freeze-drying agents, stabilizers, free radical scavengers, anti-oxidants, thiols, chelating agents, and solubilizers.

Freeze-drying agents are compounds which aid in stabilizing against the rigors of freeze-drying or storage at subzero temperatures. Illustrative freeze drying agents include sugars and amino-containing compounds. Examples include mannitol, glucose, sucrose, lactose, maltose, and trehalose; polysaccharides, such as dextrose, dextrins, and cyclodextrins; nonnatural polymers, such as polyvinylpyrrolidone (PVP); and amino acids as disclosed in U.S. Pat. No. 5,472,706.

Certain chemical compounds act as scavengers for one or more reactive species generated during sterilization, particularly irradiation. Examples of scavenger compounds include sulfites, bisulfites, mixtures of sulfites and bisulfites, ammonium sulfite salts, aminesm amides, imides, nitriles, carbamates, alcohols, mercaptans, proteins, mixtures of amines, amides, and proteins; active methylene compounds such as cyclic ketones and compounds having a β-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom. Exemplary bisulfites and sulfites include alkali metal salts such as lithium, sodium, and potassium salts, and ammonium salts, for example, sodium bisulfite, potassium bisulfite, lithium bisulfite, ammonium bisulfite, sodium sulfite, potassium sulfite, lithium sulfite, ammonium sulfite, and the like. Exemplary amines include the aliphatic and aromatic amines such as, for example, aniline, benzidine, aminopyrimidine, toluene-diamine, triethylenediamine, diphenylamine, diaminodiphenylamine, hydrazines, and hydrazide. Suitable amides include urea, cyanamide, acrylamide, benzamide, and acetamide. Suitable alcohols include phenols, 1,4-butanediol, d-sorbitol, and polyvinyl alcohol. Exemplary compounds having a dicarbonyl group include malonic acid, acetylacetone, malonamide, diethylmalonate, or other malonic esters. Cyclic ketones suitable for use in this application include cyclohexanone or cyclopentanone. Examples of heterocyclic compounds include benzimidazole, 5-methyl benzimidazole, 2-methylbenzimidazole, indole, pyrrole, 1,2,4-triazole, indoline, benzotriazole, indoline and the like.

In turning to the examples, and in particular, Examples 3, 4, 5, 6, 7, 8, and 9, and in particular, Example 6, it can be seen that the sample absent one or more stabilizing excipients exhibited a significant reduction in molecular weight upon irradiation—from 200 kilodaltons to 12 kilodaltons (a reduction of nearly 17 times or 94%). In an attempt to circumvent or ameliorate the deleterious effects of irradiation, various combinations of excipients were investigated. Preferred compositions are those comprising, in addition to a reactive polymer such as thiol-derivatized hyaluronic acid, at least one of the following stabilizing excipients: a thiol, a chelating agent, a solubilizer (such as sucrose), and an anti-oxidant. Additional illustrative compositions will comprise at least a thiol and a chelating agent, or at least a thiol and a solubilizer or at least a thiol and an anti-oxidant, or at least a chelating agent and a solubilizer, or at least a chelating agent and an anti-oxidant, or at least a solubilizer and an anti-oxidant. Further illustrative composition will comprise at least a thiol, a chelating agent and a solubilizer, or a thiol, a chelating agent and an anti-oxidant, or a chelating agent, a solubilizer and an anti-oxidant. In certain instances, the composition will comprise a thiol, a chelating agent, a solubilizer and an anti-oxidant.

Exemplary compositions include at least one of dithiothreitol, EDTA, sucrose or ascorbic acid.

Preferred compositions include at least ascorbic acid as a stabilizing excipient. Additional illustrative compositions will include, in addition to ascorbic acid, at least one of dithiothreitol, EDTA, or sucrose. For example, a composition may comprise ascorbic acid and dithiothreitol, or ascorbic acid and EDTA, or ascorbic acid and sucrose. Additional compositions are those which include ascorbic acid, dithiothreitol and EDTA, or ascorbic acid, dithiothreitol and sucrose, or ascorbic acid, sucrose and EDTA, or ascorbic acid, dithiothreitol, EDTA, and sucrose. Such compositions may optionally further include Trolox® (6-hydroxy-2,5,7,8-tetramethylchroman-2-carboxylic acid).

Preferred ranges for the foregoing excipients, relative to the thiol-functionalized hyaluronic acid, on a per weight basis, are from about $1.0 \times 10^{-3}$ to 0.10 (DTT), $2.1 \times 10^{-3}$ to 0.20 (EDTA), 0.06 to 6 (sucrose) and 0.06 to 6 (ascorbic acid).

Additional stabilizers include fatty acids, including 6,8-dimercapto-octanoic acid (lipoic acid) and its derivatives and analogues (alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, furan fatty acids, oleic and linoleic and palmitic acids and their salts and derivatives; flavonoids, phenylpropaniods, and flavenols, such as quercetin, rutin and its derivatives, apigenin, aminoflavone, catechin, hesperidin and, naringin; carotenes, including beta-carotene; Co-Q10; xanthophylls; polyhydric alcohols, such as glycerol, mannitol; sugars, such as xylose, glucose, ribose, mannose, fructose and trehalosel amino acids, such as histidine, N-acetylcysteine (NAC), glutamic acid, tryptophan, sodium carpryl N-acetyl tryptophan and methionine; azides, such as sodium azide; enzymes, such as Superoxide Dismutase (SOD) and Catalase; uric acid and its derivatives, such as 1,3-dimethyluric acid and dimethylthiourea; allopurinol; thiols, such as glutathione and cysteine; trace elements, such as selenium; vitamins, such as vitamin A, vitamin C (including its derivatives and salts such as sodium ascorbate and palmitoyl ascorbic acid) and vitamin E (and its derivatives and salts such as tocopherol acetate d-alpha tocopheryl polyethylene glycol 1000 succinate, and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin: dimethyl sulfoxide (DMSO); piperazine diethanesulfonic acid (PIPES); imidazole; methoxypsoralen (MOPS): 1,2-dithiane-4,5-diol; reducing substances, such as butylated hydroxyanisole (BHA) and butylated hydroxytoluene (BHT); cholesterol; probucol; indole derivatives; thimerosal; lazaroid and tirilazad mesylate; proanthenols; proanthacyanidins; ammonium sulfate; Pegorgotein (PEG-SOD); N-tert-butyl-alpha-phenylnitrone (PEN); o-vanillin (3-methoxy)salicylaldehyde and 4-hydroxy-2,2,6,6-tetramethylpiperidin-1-oxyl (Tempol).

Additional excipients for use in the instant compositions are described in "Handbook of Pharmaceutical Excipients", Third Ed., Ed. A.H. Kibbe, Pharmaceutical Press, 2000.

Preservatives

The compositions provided herein may also include one or more preservatives. Preservatives include anti-microbial agents, parabens, cresols, metal compounds and other known agents. For example, suitable parabens include alkyl parabens and salts thereof, such as methylparaben, methylparaben sodium, ethylparaben, propylparaben, propylparaben sodium, butylparaben, and the like. Suitable cresols include cresol, chlorocresol, and the like. A preservative may be an antimicrobial metal compounds or elemental metal including mercurial compounds, such as phenolmercuric chloride, phenolmercuric acetate, acetomeroctol, nitromersol, thimerosal, mercurochrome, mercuric chloride, and mercuric iodide; elemental metals, such as silver and copper; and metal compounds, such as copper chloride, copper sulfate, copper peptides, zinc chloride, zinc sulfate, silver nitrate, silver iodide, silver acetate, silver benzoate, silver carbonate, silver chloride, silver citrate, silver oxide, silver sulfate, and tincture of iodine. Further information on antimicrobial activities of metals can be found, for example, in S. Seymour Block, DISINFECTION, STERILIZATION AND PRESERVATION, 5$^{th}$ Ed., Philadelphia: Lippincott Williams & Wilkins, 2000, the entire disclosure of which is incorporated herein by reference.

Additional preservatives include hydroquinone, pyrocatechol, resorcinol, 4-n-hexyl resorcinol,3α,4,7,7α-tetrahydro-2-((trichloromethyl)thio)-1H-isoindole-1,3(2H)-dione, benzalkonium chloride, benzalkonium chloride solution, benzethonium chloride, benzoic acid, benzyl alcohol, cetylpyridinium chloride, chlorobutanol, dehydro acetic acid, o-phenylphenol, phenol, phenyl ethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® (diazolidinyl urea, International Specialty Products, Wayne, N.J.) and Germall 115® (imidazolidinyl urea, International Specialty Products, Wayne, N.J.).

In addition, compounds can be screened for antimicrobial and preservative properties, and selected on the basis of such screening. For example, compounds can be tested by one or more of a USP preservative test regimen, a USP microbial limits test, a USP bacteriostasis and fungistasis test, and a USP antibiotics-microbial assay. See, for example, USP 23<51>, Supplement 8, "Antimicrobial Effectiveness Testing," the entire disclosure of which is incorporated herein by reference.

A suitable preservative(s) should also be selected on the basis of compatibility. For instance, a preservative should not contribute to the decomposition of the hyaluronic acid polymer; should be compatible to the parameters of sterilizing radiation selected; and should not interfere with or prohibit the use of the sterilized composition.

The amount of preservative will depend on several factors, including, but not limited to, the amount suitable to preserve the composition, the effectiveness of the preservative, and regulatory limits imposed by the U.S. FDA or other U.S. or foreign regulatory agencies. Suitable amounts of preservatives can be determined by one of ordinary skill in the art, for example with reference to readily available resources such as S. Seymour Block, DISINFECTION, STERILIZATION AND PRESERVATION, 5$^{th}$ Ed.

Buffers

One or more buffering agents ('buffer') may also be included in the sterilized composition, and should be selected based upon the criteria discussed previously for excipients and preservatives.

Illustrative buffers include 2-amino-2-hydroxymethyl-1,3-propanediol (Tris), 2-[bis(2-hydroxyethyl)imino]-2-(hydroxymethyl)-1,3-propanediol (bis-Tris), 4-morpholine ethane sulfonic acid (MES) buffer, ammonium chloride, bicine, tricine, sodium carbonate, sodium bicarbonate, acetate, phosphate, glutamic acid, citrate, Dulbecco's phosphate-buffered saline, 4-(2-hydroxyethyl)-1-piperazineethanesulfonic acid (HEPES), methoxypsoralen (MOPS), N-cyclohexyl-3-aminopropanesulfonic acid (CAPS), N-cyclohexyl-2-hydroxyl-3-aminopropanesulfonic acid (CAPSO), N-Cyclohexyl-2-aminoethanesulfonic acid (CHES), 3-[4-(2-Hydroxyethyl)-1-piperazinyl]propanesulfonic acid (HEPPS), phosphate-buffered saline, tris-buffered saline, Hank's solution, and Ringer's solution.

Other Additives

The polymer compositions provided herein may further include one or more additional radiation stabilizing agents, such as Trolox® (described above), d-alpha tocopheryl polyethylene glycol 1000 succinate, butylated hydroxyanisole (BHA), butylated hydroxytoluene (BHT) and derivatives thereof.

The polymer composition may further include one or more crosslinking accelerants. Examples of crosslinking accelerants, also referred to in the art as initiators, include peroxides, azo compounds, persulfates, and redox initiators, generally used in an amount from about 0.01-15 wt %, or about 0.05-10 wt %, or from about 0.1-5 wt % of the polymerizable material.

Illustrative peroxide accelerants include dialkyl peroxides such as t-butyl peroxide, dicumyl peroxide, and 2,2 bis(t-butylperoxy)propane; diacyl peroxides such as benzoyl peroxide and acetyl peroxide; peresters such as t-butyl perbenzoate and t-butyl per-2-ethylhexanoate; perdicarbonates such as dicetyl peroxy dicarbonate and dicyclohexyl peroxy dicarbonate; ketone peroxides such as cyclohexanone peroxide and methylethylketone peroxide; and hydroperoxides such as cumene hydroperoxide and tert-butyl hydroperoxide. Peroxides include hydrogen peroxide, benzoyl peroxide, cumene peroxide, carbamide peroxide and potassium percarbonate. Azo accelerants include azo bis(isobutyronitrile) and azo bis (2,4-dimethylvaleronitrile). Persulfate accelerants include potassium persulfate, sodium persulfate, and ammonium persulfate.

Preferred crosslinking accelerants include hydrogen peroxide, sodium persulfate, ammonium persulfate and potassium persulfate.

Bioactive Agents

The compositions and/or kits provided herein may optionally comprise a bioactive agent. The dry sterile composition may itself comprise a bioactive agent, or alternatively, a bioactive agent may be added upon formation of the gel, or included as one component of a kit, e.g., in packaged form.

Bioactive agents that may be included in the compositions and combinations provided herein include antimicrobials, antibiotics, analgesics, antibiotics, antiproliferative/antimitotic agents including natural products such as vinca alkaloids (e.g. vinblastine, vincristine, and vinorelbine), paclitaxel, epidipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine [cladribine]); platinum coordination complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (such as brefeldin A); antiinflammatory: such as adrenocortical steroids (beclomethasone, budesonide, cortisol, cortisone, fludrocortisone, prednisone, prednisolone, methylprednisolone, betamethasone, dexamethasone, triamcinolone and salts thereof, e.g. triamcinolone diacetate, triamcinolone acetonide, triamcinolone hexacetonide), non-steroidal agents (salicylic acid derivatives e.g. aspirin); para-aminophenol derivatives, i.e. acetominophen; indole and indene acetic acids (indomethacin, sulindac, and etodolac), heteroaryl acetic acids (tolmetin, diclofenac, and ketorolac), arylpropionic acids (ibuprofen and derivatives), anthranilic acids (mefenamic acid and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive (cyclosporine, tacrolimus (FK-506), sirolimus (rapamycin), azathioprine, mycophenolate mofetil); mitogenic or morphogenic growth factor proteins, peptides or mimetics; vascular endothelial growth factor (VEGF), fibroblast growth factor (FGF), transforming growth factor-β (TGF-β) superfamily members including TGF-β's and bone morphogenic proteins (BMP's); insulin and insulin-like growth factors (IGF's), hepatocyte growth factor (HGF), epidermal growth factors (EGF's), Hedgehog proteins (SHH and IHH), activins, inhibins, demineralized bone (DBM) and platelet-derived growth factors (PDGF's), hematopoietic growth factors (G-CSF, CSF-1, GM-CSF, erythropoietin, cytokines and lymphokines including the interleukin family (IL-1 to 34)), interferons, nerve growth factors (NGF's), neutralizing, antagonist or agonist antibodies, growth factor receptor agonists or antagonists, nitric oxide donors; anti-sense oligonucleotides, transcription factors, signaling cascade mediators, and combinations thereof.

Antibiotics include antibiotics of the lincomycin family (referring to a class of antibiotic agents originally recovered from *streptomyces lincolnensis*); antibiotics of the tetracycline family (referring to a class of antibiotic agents originally recovered from *streptomyces aureofaciens*); sulfur-based antibiotics such as the sulfonamides; and so forth. Exemplary antibiotics of the lincomycin family include lincomycin itself (6,8-dideoxy-6-[[(1-methyl-4-propyl-2-pyrrolidinyl)-carbonyl]amino-]-1-thio-L-threo-□-D-galacto-octopyranoside), clindamycin, the 7-deoxy, 7-chloro derivative of lincomycin (e.g., 7-chloro-6,7,8-trideoxy-6-[[(1-methyl-4-propyl-2-pyrrolidinyl)carbonyl]amino]-1-thio-L-threo-□-D-galacto-octopyranoside), and pharmacologically acceptable salts and esters thereof. Exemplary antibiotics of the tetracycline family include tetracycline itself 4-(dimethylamino)-1,4,4α,5, 5α,6,11,12α-octahydro-3,6,12,12α-pentahydroxy-6-methyl-1,11-dioxo-2-naphthacenecarboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Antimicrobials and/or antibiotics further include compounds such as erythromycin, bacitracin, neomycin, penicillin, polymyxin B, tetracyclines, viomycin, chloromycetin and streptomycins, cefazolin, ampicillin, azactam, tobramycin, clindamycin and gentamycin.

In a preferred embodiment in which the composition or combination comprises an active agent, the active agent is a steroid.

Dry Composition

The polymer compositions provided herein are typically in dry form prior to sterilization. Typically, the compositions are prepared by mixing an aqueous solution of thiol-functionalized hyaluronic acid and excipient-containing solution, optionally containing any additional additives, stabilizers, excipients, and the like as described herein, and the pH and final solution volume adjusted as necessary.

Drying may be carried out by any of a number of methods, such as lyophilization, vacuum drying, spray freeze drying, super critical fluid processing, spray drying or other forms of evaporative drying. Preferably, the dried polymer composition is prepared by lyophilization. See, e.g., Example 3 and Example 4. Exemplary dry compositions include powders and sponges.

The biocompatible compositions can also be subjected to dehydration crosslinking treatment, such as by application of heat or addition of a crosslinking accelerant prior to drying. Advantageously, the degree of crosslinking treatment can control the decomposition time of the final gelled material, e.g., when injected or implanted in a subject.

The resulting dry polymer compositions are typically packaged as described above. Preferably, the dry composition is provided in a sealed container, such as a sealed foil pouch. In a preferred embodiment, the composition is provided in a container such as a syringe (which can be capped, optionally with a vented cap), which is then placed in a container, such as a foil pouch which is then sealed. The pouch may be vacuum sealed, sealed under an inert gas such as nitrogen or argon, or sealed following one or more vacuum/back fill cycles where the back fill gas is an inert gas such as nitrogen or argon. For the pouch sealed under one or more vacuum/back fill cycles, the cycle can be adjusted such that the pouch is finally sealed under either vacuum or an inert gas. The pouch may optionally contain a dessicant and/or an oxygen scavenger.

Terminal sterilization is carried out as described above.

Storage Stability

Terminal sterilization of a liquid or gel formulation generally does not confer the same degree of stabilization as the sterilization method of a dry composition as provided herein.

As can be seen from the supporting examples, and in particular, Example 9, the sterile dry compositions provided herein are stable under the described storage conditions for a period one week, for a period of two weeks, and for a period of at least one month. Notably, the instant sterile dry compositions remained stable not only under low temperature conditions (2-8°), but on average, appeared nearly equally stable at room temperature (25° C.). In Example 9, stability was assessed on the basis of gelation parameters, and in particular, gelation time. The gelation time of the illustrative compositions remained nearly constant, thereby indicating that neither a significant degree of crosslinking nor molecular weight degradation appeared to accompany irradiation, based upon the gelation times observed. The compositions evaluated also remained water soluble after storage, as indicated by formation of a clear solution upon wetting of the sterile, dry material, and prior to gelation. In general, a preferred dry sterile composition as provided herein, in addition to maintaining solubility in aqueous solution, possesses a gelation time following storage at 25° C. in a sealed foil pouch for a period of one month that varies by no more that ±about 25 percent, or by no more than about ±20 percent, or even by no more than about ±15 percent in comparison to the initial gelation time. For example, a dry sterile composition possesses a gelation time following storage at 25° C. in a sealed foil pouch for a period of one month that varies by no more that ±one of the following percentages: 25, 24, 23, 22, 21, 20, 19, 18, 17, 16, 15, 14, 13, 12, 11, 10, or even less.

In an alternative preferred embodiment, a preferred dry sterile composition as provided herein, in addition to maintaining its solubility in aqueous solution, comprises a thiol-derivatized hyaluronic acid having a defined weight prior to sterilization, and a molecular weight after sterilization that is within 60% of the defined molecular weight. Preferably, the molecular weight after sterilization is within about 65%, or even within 70% of the defined molecular weight. Even more preferably, the molecular weight after sterilization is within about 75%, or even within 80%, or even within 85% or even within 90% of the defined molecular weight. Both of the foregoing features are indicators, although not absolute, of a dry sterile composition that maintain its predicted performance when wetted for form a hydrogel, and in subsequent in vivo applications.

Preferably, the sterile, dry compositions provided herein are stable under storage conditions as described for a period of at least one month, and more preferably for a period of at least two months, and even more preferably, for at least three months. Ideally, the instant compositions are stable for at least six months, or even for a year or more, such as for two years. Generally, in addition to the foregoing measures, stability refers to the composition's properties, including sterility, wettability, polymerization, and gelation as maintained or measured over a period of time under particular storage conditions.

Uses

The sterile hyaluronic acid polymer compositions described herein may be used in injectable or implantable formulations, for use, e.g., embryonic development, tissue organization, wound healing, angiogenesis and tumorigenesis. See D. D. Allison and K. J. Grande-Allen, *Tissue Engineering*, Vol. 12, Number 8, 2131-2140 (2006); G. D. Prestwich et al, *Tissue Engineering*, Vol. 12, Number 8, 2171-2180 (2006); G. D. Prestwich et al, *Tissue Engineering*, Vol. 12, Number 12, 3405-3416 (2006)

For example, the compositions provided herein may be used as adhesive compositions, e.g., as tissue adhesives and sealants that may be used for various applications, including preventing bleeding, covering open wounds, and other biomedical applications. These compositions may be used in, for example, apposing surgically incised or traumatically lacerated tissues, retarding blood flow such as those from wounds, preventing restenosis or blood clotting, drug delivery; dressing burns, and aiding repair and regrowth of living tissue.

A sterile dry polymer composition as provided herein may be used for supplementing or inducing and regenerating damaged organs or tissues in a mammalian subject, such as a human. The composition is decomposed or absorbed, or alternatively, remains in the subject (e.g., mammalian subject) without having adverse influences on subject when embedded or contained therein.

Further, the sterile biocompatible compositions provided herein may additionally include bioabsorbable polymer substances such as collagen, hyaluronic acid, gelatin, and chitin, and biodegradable polymer substances such as polyester, polyamide, and polylactic acids. A sterile dry polymer composition as provided herein and when mixed with an appropriate buffer, may be used in the treatment of osteoarthritis or rheumatoid arthritis.

A sterile dry polymer composition as provided herein and when mixed with an appropriate buffer, may be used in the reduction or prevention of adhesions that can form following a surgical procedure.

A sterile dry polymer composition as provided herein and when mixed with an appropriate buffer and that contains a drug, may be used as a drug delivery system for the treatment of osteoarthritis, sinusitis, allergic rhinitis and chronic rhinosinusitis.

EMBODIMENTS

The following are illustrative embodiments.,

Kits

For example, in one embodiment, provided herein is a kit or composition comprising a sterile thiol-functionalized hyaluronic acid in dry form that is soluble in aqueous solution and one or more stabilizing excipients, optionally combined with a buffer, or preservative. The kit may further comprise a crosslinking accelerant, such as, for example, sodium persulfate, ammonium persulfate and potassium persulfate. The stabilizing excipient may be an anti-oxidant, such as ascorbic acid. In one variation of any of the disclosed embodiments, the composition further comprises a pharmaceutically active agent, such as a steroid. In a further embodiment, the steroid is selected from triamcinolone, triamcinolone diacetate, triamcinolone acetonide and triamcinolone hexacetonide. In yet another variation, the kit or composition may further comprise a crosslinker. In one variation, the linker comprises two or more methacrylate, acrylate or allyl functional groups. In yet another variation, the linker is selected from PEGDA, PEGDM, PEGDAA and PEGDMA.

Yet another embodiment, provided is a kit than includes a) a sterile dry composition that comprises a thiol-derivatized hyaluronic acid in dry form that is soluble in solution and one or more stabilizing excipients; b) optionally, a sterile composition comprising a linker, c) a container for mixing the sterile dry composition and the sterile linker composition, and d) a syringe for the injection or implantation of the solution comprising the sterile thiol-derivatized hyaluronic acid linker composition, wherein the composition is partially crosslinked. A further embodiment includes a kit comprising: a) a sterile thiol derivatized hyaluronic acid polymer in dry form that is soluble in solution b) a sterile linker composition comprising a linker, and at least one stabilizing excipient, and optionally one or more of an additional excipient, buffer, or preservative c) a container for mixing the sterile thiol-derivatized hyaluronic acid polymer and the sterile linker composition, and d) a syringe for the injection or implantation of a solution comprising a resulting sterile hyaluronic acid-linker composition, wherein the hyaluronic acid-linker complex is partially crosslinked. Preferred polymers are Carbylan™-S, Carbylan™-SX, and Carbylan™-GSX or derivatives thereof. Preferred linkers include PEGDA, PEGDM, PEGDAA, and PEGDMA. In one variation of any of the embodiments described herein, the kit further comprises a pharmaceutically active agent, which is combined with the composition before injection or implantation. In a particular embodiment, the sterile thiol-derivatized hyaluronic acid composition contains a pharmaceutically active agent.

Also provided is kit comprising: a) a container comprising a sterile dry composition comprised of a thiol-derivatized hyaluronic acid that is soluble in solution and one or more stabilizing excipients, b) a container comprising a pharmaceutically acceptable buffer; in liquid or dry form c) a container for mixing the pharmaceutically acceptable buffer with the sterile dry thiol-derivatized hyaluronic acid composition; and d) a syringe for the injection or implantation of the resulting sterile wetted composition. In one variation, the kit further comprises a pharmaceutically active agent in a separate container, which is combined with the composition before injection or implantation. In another variation, the container comprising the thiol-derivatized hyaluronic acid composition contains a pharmaceutically active agent. In one instance, a preferred pharmaceutically active agent is a steroid, such as triamcinolone, triamcinolone diacetate, triamcinolone acetonide and triamcinolone hexacetonide.

Yet another aspect is a kit for preparing a sterile composition, wherein the kit comprises: (a) a first container containing a first sterile composition comprising a thiol functionalized polysaccharide, one or more linkers, and a stabilizing excipient; (b) a second container containing a second sterile composition comprising an aqueous buffer solution. In yet another embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In a related embodiment, the syringe cap is a vented syringe cap. In one embodiment, the second container is a syringe. In one embodiment, the second container is a syringe that further comprises a syringe cap, for example a Luer tip syringe cap. In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the first container further comprises a crosslinking accelerant; in another embodiment, the second container comprises a crosslinking accelerant. In one embodiment, the crosslinking accelerant is a persulfate compound, such a persulfate compound can be selected from the group comprising ammonium persulfate, sodium persulfate and potassium persulfate. In another embodiment, the crosslinking accelerant is a peroxide. In one embodiment, the peroxide is selected from the group comprising hydrogen peroxide, benzoyl peroxide, cumene peroxide, potassium percarbonate and carbamide peroxide; in one example, the accelerant is hydrogen peroxide. In one embodiment, the aqueous buffer solution has a pH in the range 6 to 11. In one embodiment, the kit further comprises a desiccant. In one embodiment, the kit can further comprise a delivery device. In one embodiment, the delivery device is a tube, cannula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof).

In one embodiment, the linker is selected from the group comprising acrylate, allyl or methacrylate compound in which there are two or more acrylate, allyl or methacrylate groups per compound respectively. The acrylate, ally or methacrylate compounds can be small molecule or they can be polymeric in nature. In one embodiment, the linker is selected from the group comprising poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the linker is a thiol-containing compound in which the compound has two or more thiol functional groups. The thiol-containing compound can be a small molecule or polymeric in nature. In one embodiment, the thiol-containing compound can be selected from the group comprising dimercaptosuccinic acid, 2,3-dimercapto-1-propanesulfonic acid, dihydrolipoic acid, dithiol threotol, thiol functionalized dextran, and thiol-functionalized hyaluronic acid.

In yet another aspect, provided is a kit for preparing a sterile composition, wherein the kit comprises: (a) a first container containing a first sterile composition comprising a thiol functionalized polysaccharide, one or more linkers and a radiation stabilizing agent; (b) a second container containing a second sterile composition comprising an aqueous buffer solution and (c) a connector for connecting the first container and the second container to allow mixing of the 2 containers. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe that can optionally comprise a syringe cap. In one embodiment, the syringe cap is a vented syringe cap. In one embodiment, the second container is a syringe. In one embodiment, the second container is a syringe that further comprises a syringe cap, for example a Luer tip syringe cap. In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the first container further comprises a crosslinking accelerant; in another embodiment, the second container further comprises a crosslinking accelerant. In one embodiment, the crosslinking accelerant is a peroxide. In one embodiment, the peroxide is selected from the group comprising hydrogen peroxide, benzoyl peroxide, cumene peroxide, potassium percarbonate and carbamide peroxide. In one embodiment, the crosslinking accelerant is hydrogen peroxide. In one embodiment, the aqueous buffer solution has a pH in the range 6 to 11. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, cannula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof).

In one embodiment, the linker is selected from the group comprising acrylate, allyl or methacrylate compound in which there are two or more acrylate, allyl or methacrylate groups per compound respectively. In one embodiment, the acrylate, allyl or methacrylate compounds can be small molecule or they can be polymeric in nature. In one embodiment, the linker is selected from the group comprising poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the linker is a thiol-containing compound in which the compound has two or more thiol functional groups. The thiol-containing compounds can be small molecules or polymeric in nature. In one embodiment, the thiol-containing compound can be selected from the group comprising dimercaptosuccinic acid, 2,3-dimercapto-1-propanesulfonic acid, dihydrolipoic acid, dithiol threotol, thiol functionalized dextran, and thiol-functionalized hyaluronic acid.

Yet in another aspect, provided is a kit for preparing a sterile composition, wherein the kit comprises: (a) a first container containing a first sterile composition comprising a thiol functionalized polysaccharide, one or more linkers, a radiation stabilizing agent and an excipient to assist in dissolution of the thiol-functionalized polysaccharide; (b) a second container containing a second sterile composition comprising an aqueous buffer solution. In one embodiment, the thiol-functionalized polysaccharide comprises thiol-functionalized hyaluronic acid. In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. In one embodiment, the second container is a syringe. In one embodiment, the second container is a syringe that further comprises a syringe cap, for example a Luer tip syringe cap. In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the excipient to assist in dissolution is selected from the group comprising Polyethylene glycol, mono and dimethoxy-polyethylene glycol, sucrose, mannitol, amino acids and block copolymers of polyethylene glycol and polypropylene glycol (e.g. Pluronics F127 and F68). In one embodiment, the first container further comprises a crosslinking accelerant; in another embodiment, the second container further comprises a crosslinking accelerant. In one embodiment, the crosslinking accelerant is a peroxide. In one embodiment, the peroxide is selected from the group comprising hydrogen peroxide, benzoyl peroxide, cumene peroxide, potassium percarbonate and carbamide peroxide. In another embodiment, the crosslinking accelerant is hydrogen peroxide. In one embodiment, the aqueous buffer solution has a pH in the range 6 to 11. In one embodiment, the kit further comprises a connector for connecting the first container and the second container to allow mixing of the 2 containers. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, cannula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof).

In one embodiment, the linker is selected from the group comprising acrylate, allyl or methacrylate compound in which there are two or more acrylate, allyl or methacrylate groups per compound respectively. In one embodiment, the acrylate, ally or methacrylate compounds can be small molecule or they can be polymeric in nature. In one embodiment, the linker is selected from the group comprising poly(ethylene glycol)-diacrylate (PEGDA), poly(ethylene glycol)-dimethacrylate (PEGDM), poly(ethylene glycol)-diacrylamide (PEGDAA) and poly(ethylene glycol)-dimethacrylamide (PEGDMA), dextran acrylate, dextran methacrylate, dextran glycidyl methacrylate, methacrylate functionalized hyaluronic acid, acrylate functionalized hyaluronic acid, glycerol dimethacrylate, glycerol 1,3-diglycerolate diacrylate sorbitol acrylate and derivatives thereof. In one embodiment, the linker is a thiol-containing compound in which the compound has two or more thiol functional groups. The thiol-containing compound can be a small molecule or polymeric in nature. In one embodiment, the thiol-containing compound can be selected from the group comprising dimercaptosuccinic acid, 2,3-dimercapto-1-propanesulfonic acid, dihydrolipoic acid, dithiol threotol, thiol functionalized dextran, and thiol-functionalized hyaluronic acid.

Yet another aspect of the present application is a kit for preparing a sterile composition, wherein the kit comprises: (a) a first container containing a first sterile composition comprising a thiol functionalized polysaccharide, a radiation stabilizing agent and an excipient to assist in dissolution of the thiol-functionalized polysaccharide; (b) a second container containing a second sterile composition comprising an aqueous buffer solution. In one embodiment, the thiol-functionalized polysaccharide comprises thiol-functionalized hyaluronic acid.

In one embodiment, the sterile containers are glass and/or plastic; in another embodiment, the sterile containers are selected from the group consisting of ampules, vials, syringes, pipettes, tubes and applicators. In one embodiment, the container is a syringe. In one embodiment, the first container is a syringe that further comprises a syringe cap. In one embodiment, the syringe cap is a vented syringe cap. In one embodiment, the second container is a syringe. In one embodiment, the second container is a syringe that further comprises a syringe cap, for example a Luer tip syringe cap.

In one embodiment, the radiation stabilizing agent is selected from the group comprising ascorbic acid, Trolox, d-alpha tocopheryl polyethylene glycol 1000 succinate, butylated hydroxyanisole (BHA) and butylated hydroxytoluene (BHT). In one embodiment, the excipient to assist in dissolution is selected from the group comprising Polyethylene glycol, mono and dimethoxy-polyethylene glycol, sucrose, mannitol, amino acids and block copolymers of polyethylene glycol and polypropylene glycol (e.g. Pluronics F127 and F68).

In one embodiment, the first container further comprises a crosslinking accelerant. In one embodiment, the crosslinking accelerant is a peroxide. In one embodiment, the peroxide is selected from the group comprising hydrogen peroxide, benzoyl peroxide, cumene peroxide, potassium percarbonate and carbamide peroxide. In one embodiment, the second container further comprises a crosslinking accelerant. In one embodiment, the crosslinking accelerant is hydrogen peroxide. In one embodiment, the aqueous buffer solution has a pH in the range 6 to 11.

In one embodiment, the kit further comprises a connector for connecting the first container and the second container to allow mixing of the 2 containers. In one embodiment, the connector comprises a luer connector, for example a female luer connector (Female luer lug style coupler, P/N: FTLC-9002 from Value Plastics). In one embodiment, the kit further comprises a desiccant. In one embodiment, the delivery device is a tube, cannula, a needle, or a catheter. In one embodiment, the kit can be stored under conditions that are less than ambient pressure. In one embodiment, the kit can be stored under an inert atmosphere (e.g. argon, carbon dioxide, or nitrogen or a combination thereof).

Methods

A further embodiment of the present application is a method of preventing, ameliorating, or treating a defect or condition in bone, teeth nerves, cartilage, artery, soft tissue, or other tissue comprising the following steps: (a) subjecting a hyaluronic acid polymer composition as provided herein to terminal sterilization; and (b) injecting or implanting the composition, upon hydration, onto or into the bone, teeth, nerves, cartilage, blood vessels, soft tissues or other tissues. Preferably, the thiol-derivatized hyaluronic acid composition comprises one or more of ascorbic acid, ascorbate salt, DTT, EDTA, and sucrose. The composition optionally contains Trolox. In one related embodiment, the terminal sterilization comprises electron beam or gamma irradiation in an amount sufficient to sterilize the composition. In one variation of any of the disclosed embodiments, the thiol-derivatized hyaluronic acid polymer composition comprises Carbylan™-S or a derivative thereof.

In another variation, the hyaluronic acid polymer composition comprises PEGDA, PEGDM, PEGDAA, PEGDMA, or a derivative thereof.

Yet another method is provided for preparing a sterilized crosslinked polymer composition. The method comprises: a) placing a first composition into a first container; b) subjecting the first container to irradiation at a dose sufficient to sterilize the first polymeric composition; c) placing a linker composition into a second container; d) subjecting the second container to irradiation at a dose sufficient to sterilize the linker composition; and e) combining the first polymeric composition with the second polymeric composition to form a crosslinked polymeric composition. In one embodiment, the first polymeric composition comprises a polysaccharide composition; in another embodiment, the first polymeric composition comprises a thiol derivatized polysaccharide; in yet another embodiment, the first polymeric composition comprises hyaluronic acid or a conjugate thereof. In one embodiment, the first and/or second container is made of glass and/or plastic; in another embodiment, the first and/or second container is selected from the group consisting of ampules, vials, syringes, pipettes, tubes and applicators. In one embodiment, the irradiation is electron beam or gamma irradiation and has a dosage of from about 0.5-10.0 MRad; in another embodiment, the irradiation has a dosage of from about 1.5-5.0 MRad. In one embodiment, the crosslinked polymeric composition is subjected to chemical, physical or irradiation sterilization; such sterilization may include gamma irradiation, microwave irradiation, ethylene oxide, hydrogen peroxide vapor or dry heat. In one embodiment, the subjecting the first container and/or subjecting the second container to irradiation lasts for less than 1 minute.

Also provided is a method for preparing a sterilized crosslinked polymeric composition comprising the following steps: (a) placing a first polymeric composition comprising at least one stabilizing inhibitor of crosslinking into a container; (b) placing a linker composition into the container; (c) subjecting the container to sterilization; and (d) vaporizing the inhibitor of crosslinking to form a crosslinked polymer composition. In one embodiment, the first polymeric composition comprises a polysaccharide composition; in another embodiment, the first polymeric composition comprises a thiol derivatized polysaccharide. In one embodiment, the container is made of glass and/or plastic; in another embodiment, the container is selected from ampules, vials, syringes, pipettes, tubes and applicators. In one embodiment, the irradiation is electron beam or gamma irradiation and has a dosage of from about 0.5-10.0 MRad; in another embodiment, the irradiation has a dosage of from about 1.5-5.0 MRad. In yet another embodiment, the crosslinked polymeric composition is further subjected to chemical, physical or irradiation sterilization, such sterilization may include gamma irradiation, microwave irradiation, ethylene oxide, hydrogen peroxide vapor or dry heat.

Also provided is a method for preparing a sterilized crosslinked polymeric composition, comprising the following steps: a) placing a first polymeric composition into a container; b) placing a linker composition into the container; c) combining the first polymeric composition with the second polymeric composition to form a crosslinked polymeric composition; and d) subjecting the container to irradiation at a dose sufficient to sterilize the crosslinked polymeric composition. In one embodiment, the first polymeric composition comprises a polysaccharide composition; in another embodiment, the first polymeric composition comprises a thiol derivatized polysaccharide. In one embodiment, the irradiation is electron beam or gamma irradiation and has a dosage of from about 0.5-10.0 MRad; in another embodiment, the irradiation has a dosage of from about 1.5-5.0 MRad. In one embodiment, the first and/or second container is made of glass and/or plastic; in another embodiment, the first and/or second container is selected from the group consisting of ampules, vials, syringes, pipettes, tubes and applicators. In one embodiment, the product of the first polymeric composition and the linker composition is further subjected to chemical, physical or irradiation sterilization, such sterilization may include gamma irradiation, microwave irradiation, ethylene oxide, hydrogen peroxide vapor or dry heat.

Another aspect of the present application provides a method of preventing, ameliorating, or treating a defect or condition in bone, cartilage, artery, or other tissue comprising the following steps: a) subjecting a first polymeric composition to irradiation or heat sterilization; b) subjecting a linker composition to irradiation or heat sterilization; and c) combining the first polymeric composition with the linker composition to form the product of the first polymeric composition and the linker composition; d) injecting or implanting the product of the first polymeric composition and the linker composition onto the bone, cartilage, artery, or other tissue. In one embodiment, the first sterile polymeric composition comprises a polysaccharide composition; in another embodiment, the first sterile polymeric composition comprises a thiol derivatized polysaccharide; in yet another embodiment, the first sterile polymeric composition comprises hyaluronic acid or a conjugate thereof. In one embodiment, the irradiation is electron beam or gamma irradiation and has a dosage of from about 0.5-10.0 MRad; in another embodiment, the irradiation has a dosage of from about 1.5-5.0 MRad. In one embodiment, the sterile containers are glass and/or plastic; in another embodiment, the sterile containers are selected from the group consisting of ampules, vials, syringes, pipettes, tubes and applicators. In one embodiment, the method further comprises subjecting the product of the first sterile polymer composition and the linker composition to chemical, physical, or further irradiation sterilization, such sterilization may include gamma irradiation, microwave irradiation, ethylene oxide, hydrogen peroxide vapor or dry heat.
Other Also provided is a product made by the process comprising the following steps: a) placing a first polymeric composition into a first container; b) subjecting the first container to irradiation or heat sterilization; c) placing a linker composition into a second container; d) subjecting the second container to electron beam irradiation or heat sterilization; and e) combining the first polymeric composition with the linker composition to form the product of the first polymeric composition and the linker composition. In one embodiment, the first polymeric composition comprises a polysaccharide composition; in another embodiment, the first polymeric composition comprises a thiol derivatized polysaccharide; in yet another embodiment, the first polymeric composition comprises a thiol-derivatized hyaluronic acid. In one embodiment, the sterilized crosslinked polymeric composition is used in the manufacture of a medicament for the treatment of a disease or condition of bone, teeth, soft tissue, arteries, nerves, and/or cartilage.

The present application is further directed to the use of the sterilized non-crosslinked and partially crosslinked and crosslinked hyaluronic acid compositions as provided herein in the manufacture of a medicament for the treatment of a disease or condition of bone, tissue, arteries, eyes, skin, and/or cartilage.

In one aspect of any of the above embodiments, the sterilized hyaluronic acid composition comprises Carbylan™-S or derivatives thereof, and one or more stabilizing excipients, optionally combined with a buffer or preservative. In another aspect, sterilized hyaluronic acid composition comprises Carbylan™-SX or derivatives thereof, and optionally one or more of an excipient, buffer, or preservative. In yet another aspect, sterilized hyaluronic acid composition comprises Carbylan™-GSX or derivatives thereof, and optionally one or more of an excipient, buffer, or preservative.

In any one or more of the above embodiments, where applicable, the electron beam irradiation has a dosage of from about 0.5-10.0 MRad (5-100 kGy). In another embodiment, the electron beam irradiation has a dosage of from about 1.5-5.0 MRad (15-50 kGy) or 2-3 MRad (20-30 kGy). In yet another embodiment, the electron beam irradiation lasts for less than 5 minutes, or lasts for less than 1 minute. Alternatively, the electron beam irradiation lasts for less than 10 seconds. In certain embodiments, the temperature of the sterilization procedure is at about 2 to 50° C., or about 15 to 40° C., about 20 to 35° C., or about 20 to 30° C., about 20 to 25° C., or about 25 to 30° C.

In any one or more of the above embodiments, where applicable, the gamma irradiation has a dosage of from about 0.5-10.0 MRad (5-100 kGy). In another embodiment, the gamma irradiation has a dosage of from about 1.5-5.0 MRad (15-50 kGy) or 2-3 MRad (20-30 kGy). Such sterilization can be carried out over a period of time, for example, about 1 minute or less to about 24 hours. In yet another embodiment, the gamma irradiation lasts for less than 5 minutes, alternatively, the gamma irradiation lasts for less than 1 minute, or for less than 10 seconds. In yet additional embodiments, the temperature of the sterilization procedure may be about 2 to 50° C., or about 15 to 40° C., about 20 to 35° C., or about 20 to 30° C., about 20 to 25° C., or about 25 to 30° C.

Depending on the particular compositions employed or the method for preparing any compositions of the present invention, the variables, parameters and conditions described herein may be used interchangeably to optimize the compositions and/or the methods herein. For example, a composition described as using a particular polymer composition that is Carbylan™-S with a particular sterilization condition such as with an electron beam irradiation with a dosage of from about 0.5-10.0 MRad (5-100 kGy), for example, may be used interchangeably with a different polymer composition with an electron beam irradiation with a dosage of from about 0.5-10.0 MRad (5-100 kGy), with or without the addition of excipients (other than the one or more stabilizing excipients), or other additives or as described herein.

The present application will now be described in connection with certain embodiments, which are not intended to limit the scope of the invention. On the contrary, the present application covers all alternatives, modifications, and equivalents as included within the scope of the claims. Thus, the following will illustrate the practice of the present application, for the purposes of illustration of certain embodiments and is presented to provide what is believed to be a useful and readily understood description of its procedures and conceptual aspects.

EXAMPLES

The following examples are put forth to provide those of ordinary skill in the art with a complete disclosure and description of how the compounds, compositions, and methods provided herein are made and evaluated, and are intended to be purely exemplary. Thus, the examples are in no way intended to limit the scope of what the inventors regard as their invention. There are numerous variations and combinations of reaction conditions, e.g., component concentrations, desired solvents, solvent mixtures, temperatures, pressures, and other reaction parameters and conditions that may be employed to optimize product characteristics such as purity, yield, and the like. Such are considered as well within the scope of the present disclosure.

Materials and Methods

Materials

CM-HA or Carbylan™: The structure, synthesis and characterization of carboxymethyl hyaluronic acid
is described in International Patent Publication No. 2005/056608 (FIG. 5 and Example 3).

CM-HA-DTPH or Carbylan™-S: The structure, synthesis, and characterization of carboxymethyl-hyaluronic acid-dithiobis(propanoic dihydrazide is described in International Patent Publication No. 2005/056608 (FIG. 5 and Example 4).

Carbylan™-SX and Carbylan™-GSX hydrogels: The preparation of Carbylan™-SX and Carbylan™-GSX hydrogels by crosslinking of Carbylan™-S and Gelatin-DTPH with PEGDA (poly(ethylene glycol)diacrylate) is also described in International Patent Publication No. 2005/056608 (FIG. 8 and Example 6).

Example 1

Dynamic Mechanical Properties of Carbylan™-SX Post-Sterilization

The gelation of hydrogels with varying linker lengths, crosslinking ratios and concentrations are qualitatively examined after sterilization using dynamic rheology (Model AR550; TA Instruments; New Castle, Del.) according to ASTM D4473-01. It is expected that under the sterilization conditions described herein, the dynamic mechanical properties of the Carbylan™-SX are not changed significantly post-sterilization when compared to the dynamic mechanical properties pre-sterilization.

The response of the hydrogel to the applied stress is measured and the storage modulus (G'), loss modulus (G") and dynamic viscosity (η*) are examined over time. Gel point is defined as the time at which the storage modulus (G') and loss modulus (G") curves cross and where there is a dramatic increase in complex viscosity, representing a change in hydrogel behavior from more viscous to more elastic.

For this study, a parallel plate set up is used with 20 mm diameter plates and a 0.8 mm gap. The Carbylan™-S and PEDGA are vortex mixed and the suspension is immediately placed on the Teflon plate of the rheometer. The stainless steel parallel plate geometry is lowered approximately 2 mm into the sample, and time-dependent changes in G', G" and η* are recorded during an oscillatory controlled stress experiment with a time sweep. All tests are performed at room temperature under a controlled frequency of 1 Hz and 0.25% strain to avoid destroying sample structure. The crossover of the G' and G" curves as well as the slope of the complex viscosity curve are analyzed using Rheology Advantage Data Analysis software (v4.1.2; TA Instruments).

Under the sterilization conditions described herein, the response of the Carbylan™-S hydrogels to the applied stress does not significantly change before the sterilization when compared to the response after the sterilization process. The gel point ranges from approximately 10 minutes to almost 170 minutes. Higher molecular weights for both the starting material, Carbylan™-S, and crosslinker, PEGDA, generally result in materials with a faster gel time.

Example 2

Enzymatic degradation in vitro of Carbylan™-SX Hydrogel Pre and Post-Sterilization A 1.25% (w/v) solution of Carbylan™-S was prepared in DPBS, and then the solution pH was adjusted to 7.4 by adding 0.1 N NaOH. Carbylan™-SX hydrogel was prepared in a petri dish (3.5 cm in diameter) by adding 1.2 ml 4.5% (w/v) PEGDA in DPBS to 4.8 ml of an aqueous Carbylan™-S solution. The hydrogel was allowed to react to completion over a time course of from 4-12 hours. A 3.0-mm diameter biopsy punch was then used to cut a cylindrical piece of hydrogel from the gel in a petri dish. This disc was placed into a small glass vial containing 2.0 ml of hyaluronidase (HAse) solutions (0, 0.5 U/ml, 2 U/ml and 20 U/ml) that were prepared in 30 mM citric acid, 150 mM $Na_2HPO_4$, 150 mM NaCl (pH 6.3). The vials were incubated at 37° C. with orbital agitation at 150 rpm. The weight of each sample was monitored using a digital scale and is measured every 24 hrs for 5 days. The samples were removed from the incubator and the enzyme solution is discarded. The hydrogel cylinders were then placed on filter paper and allowed to blot dry for several seconds. The samples were then weighed using a digital scale and returned to the glass vial with fresh HAse solution.

The weight loss fraction is defined as $1-Wt/Wo$, where Wt is the weight of the sample at time t and Wo is the original weight of the sample. The values for the weight loss percent are plotted as a function of time. The results indicated that the digestion is dependent on enzyme concentration. After 5 days at 37° C. with gentle agitation, ca. 63% of the hydrogel was digested at the highest HAse concentration (20 U/ml) employed. No significant degradation occurred in the absence of added HAse.

Carbylan™-SX is slowly hydrolyzed in vivo and the degradation rate is similar to that found previously for PEGDA-crosslinked HA-DTPH.

When the same experiments are conducted on Carbylan™-SX after a sterilization procedure, it is expected that no significant difference is observed in the rate of hydrolysis when compared to unsterilized Carbylan™-SX.

Example 3

Preparation of Lyophilized Thiol-Functionalized Hyaluronic Acid with Excipients

Excipient stock solution was prepared by mixing 2 ml of 500 mM EDTA, 10 g of ascorbic acid, 10 g of sucrose, and 154.25 mg DTT in 100 ml of 10×PBS until complete dissolution. 875 mL of a Carbylan™-S solution (20 mg/ml) was mixed with the excipient stock (100 mL). The final Carbylan™-S/excipient volume was adjusted to 1 liter by addition of deionized $H_2O$. The pH was adjusted to 3.0 by addition of 6N NaOH. The Carbylan™-S/Excipient solution was then mixed with 250 ml of 40 mg/ml PEG4000. A volume of 3 ml of Carbylan™-S/PEG4000 solution was then dispensed into a 3 ml×100 Teflon mold using a repeater pump. The Carbylan™-S/PEG4000 excipient solution was lyophilized with a 34 hour cycle using Millrock lyophilizer. The resulting sponges were placed in 5 ml plastic syringes, pouched with a $N_2$/vacuum cycle and desiccants in foil pouches, and finally treated with e-beam sterilization.

Example 4

Preparation of Lyophilized Thiol Functionalized Hyaluronic Acid with Excipients and Steroid An excipient stock solution was prepared by adding 2 ml of 500 mM EDTA, 10 g of ascorbic acid, 10 g of sucrose, and 154.25 mg DTT to 100 ml of 10×PBS until complete dissolution. 875 mL of a Carbylan™-S solution (20 mg/ml) was added to the excipient stock (100 mL). The final Carbylan™-

S/excipient volume was adjusted to 1 liter with Di H$_2$O. The pH was then adjusted to 3.0 by addition of 6N NaOH. The Carbylan™-S/Excipient solution was then mixed with 250 ml chromatography. A summary of the excipients used and the M$_w$ of the Carbylan™-S pre- and post-irradiation are provided in the table below:

TABLE 1

M$_w$ OF CARBYLYN ™-S AFTER STERILIZATION IN THE PRESENCE OF IDENTIFIED EXCIPIENTS

| # | Carb-S (mg) | DTT (mg) | EDTA (mg) | Trolox (mg) | Sucrose (mg) | AA (mg) | Method of sterilization | Dose (KGy) | Formulation | Pre-sterilization MW (kD) | Post-Sterilization MW (kD) | Sponge dissolved |
|---|---|---|---|---|---|---|---|---|---|---|---|---|
| 1 | 42 | 0 | 0 | 0 | 0 | 0 | gamma | 20 | Carb-S | 200 | 12 | No |
| 2 | 42 | 0.370 | 0.893 | 0.24 | 216 | 0 | e-beam | 20 | Carb-S | 235 | 103 | Yes |
| 3 | 42 | 0.370 | 0.893 | 0.24 | 216 | 0 | gamma | 20 | Carb-S | 243 | 101 | Yes |
| 4 | 35 | 0.308 | 0.744 | 0.200 | 180 | 0 | e-beam | 20 | Carb-S | 243 | 121 | Yes |
| 5 | 35 | 0.308 | 0.744 | 0.200 | 180 | 0 | gamma | 20 | Carb-S | 237 | 123 | Yes |
| 6 | 28 | 0.247 | 0.595 | 0 | 16 | 16 | e-beam | 20 | Carb-SX | 228 | 228 | Yes |
| 7 | 42 | 0.370 | 0.893 | 0 | 24 | 24 | e-beam | 20 | Carb-S | 230 | 161 | Yes | of 40 mg/ml PEG4000. An equivalent of 10 mg triamcinolone acetonide per 3 mL solution was then added to the solution. A volume of 3 ml of Carbylan™-S/PEG4000/excipient/triamcinolone solution was dispensed into a 3 ml×100 Teflon mold using a repeater pump. The Carbylan™-S/PEG4000/excipient/triamcinolone was lyophilized with a 34 hour cycle using Millrock lyophilizer. The resulting sponges were placed in 5 ml plastic syringes, pouched with a N$_2$/vacuum cycle and desiccants in foil pouches, and finally treated with e-beam sterilization.

Example 5

Terminal Sterilization Methods

Gamma Irradiation. Lyophilized thiol-functionalized hyaluronic acid-containing samples as described herein were taken to a commercial irradiation facility and were irradiated at ambient temperature (20-25° C.) to a total dose between about 12 kGy and about 50 kGy each. The radiation dose is assessed by dosimeters attached to the vial and by an external dosimeter placed in close proximity to the vial. The residual colony forming units (CFUs) are counted for each vial; killing of bioindicators are achieved over multiple experimental evaluations.

Electron beam sterilization: Lyophilized thiol-functionalized hyaluronic acid-containing samples as described herein were taken to a commercial irradiation facility and irradiated at ambient temperature (20-25° C.) to a total dose of between about 12 kGy and about 50 kGy. The radiation dose is assessed by an external dosimeter placed in close proximity to the sample.

Example 6

Effect of Excipients on Carbylan™-S Molecular Weight During Sterilization

A series of Carbylan™-S sponges with various excipients was prepared as generally described in Example 3. The molecular weight (M$_w$) of the Carbylan™-S sponges were measured using gel permeation chromatography (Agilent Series 1100 HPLC with Wyatt RI (Optilab Rex) and LS detector (Dawn EOS), Column: Shodex OHPak (SB-806M HQ), solvent: 50 mM NaHPO$_4$, pH 6.5). The sponges were then irradiated with approx 25 kGy electron beam radiation. Following irradiation, the sponges were dissolved in deionized water and M$_w$ was measured again using gel permeation The data show that the addition of certain excipients of the type described herein protects the exemplary sterile thiol-functionalized hyaluronic acid, sterile Carbylan™-S, and reduces the effect of the electron beam radiation on reducing the molecular weight of the polymer. The preferred combination and concentration of excipients in sample 6 appears, based upon the samples examined, to best preserve the pre-irradiation M$_w$ properties of the Carbylan™-S component, an important parameter for the function of Carbylan™-S based formulations. Looking at Table 1, it can be seen that in sample 6 the amounts of the various excipients relative to the Carbylan™-S, on a per weight basis, is as follows: $9.0 \times 10^{-3}$ (DTT), $2.1 \times 10^{-2}$ (EDTA), 0.58 (sucrose) and 0.58 (ascorbic acid). Preferred ranges for such excipients, relative to the thiol-functionalized hyaluronic acid, are from about $1.0 \times 10^{-3}$ to 0.10 (DTT), $2.1 \times 10^{-3}$ to 0.20 (EDTA), 0.06 to 6 (sucrose) and 0.06 to 6 (ascorbic acid).

Example 7

Testing of Materials Following Sterilization—Formulation 1

A lyophilized sponge was prepared in a similar manner to that described in Example 3. The sponge contained 75 mg Carb-S, 0.89 g ethylenediaminetetraacetic acid disodium salt, 3.6 mg Na$_2$HPO$_4$, 24 mg sucrose, 24 mg ascorbic acid, 0.37 mg dithiothreitol, 24 mg poly(ethylene glycol)-3350, 30 mg cysteine hydrochloride monohydrate and 0.93 mg NaH$_2$PO$_4$-dihydrate. This lyophilized sponge was placed in a syringe that contained 1.5 mg sodium persulfate. The plungers were inserted and pushed down until the plunger almost touched the sponge. A vented syringe cap was placed on the tip of the syringe. The syringe was pouched in a foil pouch. A desiccant and oxygen scavenger were added to the foil pouch. The foil pouch was then subjected to 3×N$_2$/vacuum cycles after which the foil pouch was heat sealed. The foil pouches terminally sterilized (e-beam) at different doses.

A syringe containing a sponge was removed from the foil pouch. A syringe containing 2 mL 0.17M sodium phosphate (pH 7.4) was connected to the sponge—containing syringe using a female-female luer connector (Value Plastics, Cat# FTLC-9002). The buffer solution was pushed into the sponge—containing syringe by depressing the plunger of the buffer syringe. A timer was then started to measure the time that had elapsed. The sponge buffer was then transferred to the buffer syringe by depressing the plunger of the sponge containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector. The contents of the syringe were then assessed as to whether they had dissolved. Dissolution of Carb-S Sponges refers to the ability of the dry material to be wetted with gelation buffer and become a liquid. Once in the liquid state, the material may be a clear solution (passing), a cloudy solution, a clear gel, or a cloudy and gray gel (failing). Once the determination had been made on whether the material had dissolved, the contents of the syringe were expelled into a plastic weigh boat and assessed for gelation.

Gelation of Carb-S Sponges refers to the change in physical state from liquid to gel. The sponge has become a gel when the material can be picked up from the holding vessel as a single piece. A pipette tip was placed into the material and was used to lift the material from the weigh boat. The gelation time was the elapsed time from when the timer was started to when the material was able to be picked up as a single piece with the pipette tip.

The gel times obtained are shown below:

TABLE 2

| Formulation | E-beam Dose (KGy) | Dissolved | Gel Time (min:sec) |
|---|---|---|---|
| 1 (NB37:18 AV) | 20 | Yes | 12:57 |
| 1 (NB37:18 AV) | 25 | Yes | 12:45 |
| 1 (NB37:18 AV) | 30 | Yes | 13:33 |

The dissolution of the sponges demonstrates that the increasing e-beam dose did not cause significant crosslinking of the material prior to gelation. The gel times were similar showing that the increasing dose of e-beam radiation did not dramatically alter the gel times for the materials.

Example 8

Testing of Materials Following Sterilization—Formulation 2

A lyophilized sponge was prepared in a similar manner to that described in Example 3. The sponge contained 75 mg Carb-S, 0.89 g ethylenediaminetetraacetic acid disodium salt, 3.6 mg $Na_2HPO_4$, 24 mg sucrose, 24 mg ascorbic acid, 0.37 mg dithiothreitol, 24 mg poly(ethylene glycol)-3350, 30 mg cysteine hydrochloride monohydrate and 0.93 mg $NaH_2PO_4$-dihydrate. This lyophilized sponge was placed in a syringe that contained 3 mg sodium persulfate. The plungers were inserted and pushed down until the plunger almost touched the sponge. A vented syringe cap was placed on the tip of the syringe. The syringe is pouched in a foil pouch. A desiccant and oxygen scavenger was added to the foil pouch. The foil pouch was then subjected to 3×$N_2$/vacuum cycles after which the foil pouch was heat sealed. The foil pouches terminally sterilized (e-beam) at different doses.

A syringe containing a sponge was removed from the foil pouch. A syringe containing 2 mL 0.17M sodium phosphate (pH 7.4) was connected to the sponge containing syringe using a female-female luer connector (Value Plastics, Cat# FTLC-9002). The buffer solution was pushed into the sponge-containing syringe by depressing the plunger of the buffer syringe. A timer was then started to measure the time that had elapsed. The sponge buffer was then transferred to the buffer syringe by depressing the plunger of the sponge containing syringe. This process was repeated 20 times. The empty syringe was removed the luer connector and a syringe containing 1 mL saline was connected to the luer connector. The saline was then mixed with the contents of the syringe. The mixture was passed back and forth 10 times. The syringe containing the resultant solution was removed from the luer connector. The contents of the syringe were then assessed as to whether they had dissolved. Dissolution of Carb-S Sponges refers to the ability of the dry material to be wetted with gelation buffer and become a liquid. Once in the liquid state, the material may be a clear solution (passing), a cloudy solution, a clear gel, or a cloudy and gray gel (failing). Once the determination had been made on whether the material had dissolved, the contents of the syringe were expelled into a plastic weigh boat and assessed for gelation.

Gelation of Carb-S Sponges refers to the change in physical state from liquid to gel. The sponge has become a gel when the material can be picked up from the holding vessel as a single piece. A pipette tip was placed into the material and was used to lift the material from the weigh boat. The gelation time was the elapsed time from when the timer was started to when the material was able to be picked up as a single piece with the pipette tip.

The gel times obtained are shown below:

TABLE 3

| Formulation | E-beam Dose (KGy) | Dissolved | Gel Time (min:sec) |
|---|---|---|---|
| 2 (NB37:18 AC) | 20 | Yes | 12:57 |
| 2 (NB37:18 AC) | 25 | Yes | 12:45 |
| 2 (NB37:18 AC) | 30 | Yes | 13:33 |

The dissolution of the sponges shows that the increasing e-beam dose did not cause crosslinking of the material prior to gelation. The gel times were similar showing that the increasing dose of e-beam radiation did not dramatically alter the gel times for the materials.

Example 9

Stability of Sterilized Product—Effect of E-beam Dose

Samples for the stability testing were prepared as described in Example 8. The sterilized sponges were stored at either of the following temperature ranges: 2-8° C. and 25° C. following sterilization. At specific time points the dissolution and gel time of the material was determined (as described in Example 9). The data obtained is shown in the table below.

TABLE 4

Summary of Stability data for Formulation NB31:116A AV

| Sample | E-beam Dose (KGy) | Gel time (T = 0) [Min:sec] | Gel time (1 Week) [Min:sec] | | Gel time (2 Weeks) [Min:sec] | | Gel time (1 Month) [Min:sec] | |
|---|---|---|---|---|---|---|---|---|
| | | | 2-8° C. | 25° C. | 2-8° C. | 25° C. | 2-8° C. | 25° C. |
| NB31:116A AV | 21 kGy | 9:14 | 8:30 | 9:11 | 9:09 | 9:39 | 8:19 | 8:02 |
| NB31:116A AV | 28 kGy | 8:40 | 8:09 | 9:06 | 8:44 | 9:13 | 8:01 | 8:39 |
| NB31:116A AV | 31 kGy | 8:42 | 8:29 | 9:11 | 9:53 | 9:09 | 8:23 | 8:34 |

The data in Table 4 illustrates that the materials are stable following e-beam sterilization at different e-beam doses over an extended period of time as indicated by reproducible gel times over a period of one month—under both low temperature conditions and at room temperature.

Adverse effects of irradiation on gelation of the illustrative dry compositions generally manifests as either an inability to gel or premature gelation that would prevent dissolution of the sterilized compositions. For example, degradation of the sterilized material can occur over time in the presence of residual radicals or other active species, resulting in an increase in gel time due to degradation of the polymer. Alternatively, a decrease in gel time can occur in the presence of residual radicals or other reactive species due to crosslinking reactions.

Since neither a significant increase nor decrease in gelation times was observed over time, it can be seen that the subject sterile materials are stable upon preparation, as well as over time.

Example 10

Testing of Materials for Sterility

A lyophilized sponge was prepared in a similar manner to that described in Example 3. The sponge contained 75 mg Carb-S, 0.89 g ethylenediaminetetraacetic acid disodium salt, 3.6 mg $Na_2HPO_4$, 24 mg sucrose, 24 mg ascorbic acid, 0.37 mg dithiothreitol, 24 mg poly(ethylene glycol)-3350, 30 mg cysteine hydrochloride monohydrate and 0.93 mg $NaH_2PO_4$-dihydrate. The lyophilized sponge was placed in a syringe that contained 3 mg sodium persulfate. The plungers were inserted and pushed down until the plunger almost touched the sponge. A vented syringe cap was placed on the tip of the syringe. The syringe is pouched in a foil pouch. A desiccant and oxygen scavenger was added to the foil pouch. The foil pouch was then subjected to $3 \times N_2$/vacuum cycles after which the foil pouch was heat sealed. The foil pouches terminally sterilized (e-beam) at approx 12 KGy. The irradiated samples were tested for sterility using the USP sterility test. These tests were conducted at Apptec (St. Paul, Minn.; Test code 1105000, Procedure # BS510CBY.201). At 14 days, 10 of 10 test samples had no positive growth showing that the materials were sterile.

It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims. Any combination of the above-described elements in all possible variations thereof is encompassed by the invention unless otherwise indicated herein or otherwise clearly contradicted by context.

What is claimed:

1. A sterile dry polymer composition prepared by terminal sterilizing irradiation and that is soluble in aqueous solution, said composition comprising a thiol-derivatized hyaluronic acid and stabilizing excipients selected from ascorbic acid, and at least one of dithiothreitol, ethylenediamine tetraacetic acid (EDTA), or sucrose, wherein said thiol-derivatized hyaluronic acid has a molecular weight in the range of 50,000 daltons to 1,000,000 daltons as determined by multi-angle light scattering and is capable of crosslinking to form a hydrogel wherein significant cross-linking due to the terminal stabilizing radiation is inhibited by the presence of the stabilizers in the composition.

2. The sterile dry polymer composition of claim 1, wherein the thiol-derivatized hyaluronic acid has a defined molecular weight prior to sterilization, and a molecular weight after sterilization by 20 kGy irradiation that is within 60% of the defined molecular weight.

3. The sterile dry polymer composition of claim 1 or claim 2, comprising dithiothreitol and ethylenediamine tetraacetic acid in addition to ascorbic acid.

4. The sterile dry polymer composition of claim 3, further comprising sucrose.

5. The sterile dry polymer composition of claim 1 or 2, comprising one or more of the following amounts of stabilizing excipient on a per weight basis relative to the thiol-derivatized hyaluronic acid: from about $1.0 \times 10^{-3}$ to 0.10 times dithiothreitol, from about $2.1 \times 10^{-3}$ to 0.20 times EDTA, from about 0.06 to 6 times sucrose, and from about 0.06 to 6 times ascorbic acid.

6. The sterile dry polymer composition of claim 1, wherein said composition possesses an initial gelation time that changes by no more than about ±25% upon storage at 25° C. in a sealed foil pouch for a period of one month.

7. The sterile dry polymer composition of claim 6, comprising one or more of the following amounts of stabilizing excipient on a per weight basis relative to the thiol-derivatized hyaluronic acid: from about $1.0 \times 10^{-3}$ to 0.10 times dithiothreitol, from about $2.1 \times 10^{-3}$ to 0.20 times EDTA, from about 0.06 to 6 times sucrose, and from about 0.06 to 6 times ascorbic acid.

8. The sterile dry polymer composition of any one of claims 1, 2, or 6, wherein the thiol-derivatized hyaluronic acid is carboxymethyl-hyaluronic acid-dithiobis(propanoic dihydrazide) (CM-HA-DTPH).

9. The sterile dry polymer composition of any one of claims 1, 2, or 6, wherein the thiol-derivatized hyaluronic acid is not crosslinked or is lightly crosslinked.

10. The sterile dry polymer composition of any one of claims 1, 2, or 6, wherein the thiol-derivatized hyaluronic acid has a molecular weight ranging from about 90,000 daltons to about 300,000 daltons.

11. The sterile dry polymer composition of claim 1 in an electron-beam or gamma ray-permeable container.

12. A method for forming the sterile dry polymer composition of claim 4, said method comprising:
providing a sealed container comprising a dry polymer composition comprised of a thiol-derivatized hyaluronic acid, ascorbic acid, dithiothreitol, ethylenediamine tetraacetic acid (EDTA), or sucrose, wherein said composition possesses an initial gelation time, and
subjecting the sealed container to electron beam or gamma irradiation at a dose and under conditions sufficient to sterilize the contents of said sealed container, to thereby provide a sterile dry polymer composition that is (i) soluble in aqueous solution and is capable of crosslinking to form a hydrogel, and (ii) possesses a gelation time that is changed by no more than about ±25% upon storage at 25° C. in a sealed foil pouch for a period of one month.

13. A method for forming the sterile dry polymer composition of claim 1, said method comprising:
providing a sealed container comprising a dry polymer composition comprised of a thiol-derivatized hyaluronic acid and stabilizing excipients selected from ascorbic acid and at least one of dithiothreitol, ethylenediamine tetraacetic acid (EDTA), or sucrose, wherein said thiol-derivatized hyaluronic acid has a defined molecular weight as determined by multi-angle light scattering, and subjecting the sealed container to electron beam or gamma irradiation at a dose and under conditions sufficient to sterilize the contents of said sealed container, to thereby provide a sterile dry polymer composition that is soluble in aqueous solution and is capable of crosslinking to form a hydrogel, wherein the defined molecular weight of the thiol derivatized hyaluronic acid is in the range of 50,000 daltons to 1,000,000 daltons.

14. The method of claim 13, wherein the thiol-derivatized hyaluronic acid has a molecular weight after sterilization by irradiation that is within 60% of the defined molecular weight prior to sterilization.

15. The method of any one of claims 13-12, wherein said irradiation is electron beam irradiation at a dosage ranging from 0.5 to 10.0 MRad.

16. The method of claim 15, wherein the electron beam irradiation dosage ranges from about 1.5 to 5.0 MRad.

17. The method of any one of claims 13-12, wherein said irradiation is gamma irradiation at a dosage ranging from about 0.5-10.0 MRad.

18. The method of claim 17, wherein the gamma irradiation is in a dosage range from about 1.5 to 5.0 MRad.

19. The method of any one of claims 13-12 wherein said thiol-derivatized hyaluronic acid polymer is selected from carboxymethyl-hyaluronic acid-dithiobis(propanoic dihydrazide.

20. A method for forming a hydrogel suitable for injecting or implanting onto bone, teeth, nerves, cartilage, artery, soft tissues or other tissues of a mammalian subject by mixing the sterile dry powder of claim 1 with a pharmaceutically acceptable buffer solution.

* * * * *

UNITED STATES PATENT AND TRADEMARK OFFICE
CERTIFICATE OF CORRECTION

PATENT NO. : 9,011,894 B2
APPLICATION NO. : 12/165607
DATED : April 21, 2015
INVENTOR(S) : Daniloff et al.

It is certified that error appears in the above-identified patent and that said Letters Patent is hereby corrected as shown below:

In the claims,

Column 39, claim 15: change "The method of any one of claims 13-12, wherein said irradiation is electron beam irradiation at a dosage ranging from 0.5 to 10.0 MRad." to --The method of any one of claims 12-14, wherein said irradiation is electron beam irradiation at a dosage ranging from 0.5 to 10.0 MRad.--

Column 39, claim 17: change "The method of any one of claims 13-12, wherein said irradiation is gamma irradiation at a dosage ranging from about 0.5-10.0 MRad." to --The method of any one of claims 12-14, wherein said irradiation is gamma irradiation at a dosage ranging from about 0.5-10.0 MRad.--

Column 39, claim 19: change "The method of any one of claims 13-12 wherein said thiol-derivatized hyaluronic acid polymer is selected from carboxymethyl-hyaluronic acid-dithiobis(propanoic dihydrazide)." to --The method of any one of claims 12-14, wherein said thiol-derivatized hyaluronic acid polymer is selected from carboxymethyl-hyaluronic acid-dithiobis(propanoic dihydrazide).--

Column 31, line 7 through 10: change: "CM-HA-DTPH or Carbylan.TM.-S: The structure, synthesis, and characterization of carboxymethyl-hyaluronic acid-dithiobis(propanoic dihydrazide is described in International Patent Publication No. 2005/056608 (FIG. 5 and Example 4)." to --CM-HA-DTPH or Carbylan.TM.-S: The structure, synthesis, and characterization of carboxymethyl-hyaluronic acid-dithiobis(propanoic dihydrazide) is described in International Patent Publication No. 2005/056608 (FIG. 5 and Example 4).--

Signed and Sealed this
First Day of March, 2016

Michelle K. Lee
*Director of the United States Patent and Trademark Office*